(12) United States Patent
Hahn et al.

(10) Patent No.: US 12,109,212 B2
(45) Date of Patent: *Oct. 8, 2024

(54) METHODS OF TREATING CANCER HAVING AN ACTIVE Wnt/β-CATENIN PATHWAY

(71) Applicant: Dana-Farber Cancer Institute, Inc., Boston, MA (US)

(72) Inventors: William C. Hahn, Newton, MA (US); Joseph Rosenbluh, Brookline, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/550,993

(22) Filed: Aug. 26, 2019

(65) Prior Publication Data
US 2020/0101070 A1    Apr. 2, 2020

Related U.S. Application Data

(62) Division of application No. 14/389,310, filed as application No. PCT/US2013/030889 on Mar. 13, 2013, now Pat. No. 10,426,774.

(60) Provisional application No. 61/618,027, filed on Mar. 30, 2012.

(51) Int. Cl.
| | |
|---|---|
| *A61K 31/506* | (2006.01) |
| *A61K 45/06* | (2006.01) |
| *C07K 14/47* | (2006.01) |
| *C12N 15/113* | (2010.01) |
| *G01N 33/50* | (2006.01) |

(52) U.S. Cl.
CPC ............ *A61K 31/506* (2013.01); *A61K 45/06* (2013.01); *C07K 14/47* (2013.01); *C07K 14/4702* (2013.01); *C07K 14/4747* (2013.01); *C12N 15/1135* (2013.01); *G01N 33/5017* (2013.01); *C12N 2310/14* (2013.01); *C12N 2310/3233* (2013.01); *C12N 2310/531* (2013.01); *G01N 2500/10* (2013.01)

(58) Field of Classification Search
CPC .................................................. A61K 31/506
See application file for complete search history.

(56) References Cited

U.S. PATENT DOCUMENTS

| 10,426,774 B2 | 10/2019 | Hahn et al. |
| 2015/0065518 A1 | 3/2015 | Hahn et al. |

FOREIGN PATENT DOCUMENTS

| KR | 20110135018 | 12/2011 | |
| KR | 20110135018 A | * 12/2011 | |

OTHER PUBLICATIONS

Luu et al. Current Cancer Drug Targets (2004), vol. 4(8), pp. 653-671.*
Konecny et al., British Journal of Cancer (2009) 101, 1699-1708.*
Lee et al., Cancer Research and Treatment, vol. 36, No. 4, Jan. 1, 2004 (p. 246).*
Ruben Abagyan, "Mitoxantrone Information," Jan.-Mar. 2022, obtained from <http://ruben.ucsd.edu/dnet/drug_html/mitoxantrone.html> Accessed Mar. 12, 2022.*
Stein et al., British Journal of Cancer (2012) 106, 1395-1405.*
Chan et al., Oncology Letters 3: 807-815 (2012).*
Bilal et al, "Identification of the YES1 Kinase as a Therapeutic Target in Basal-Like Breast Cancers," Genes & Cancer, Oct. 2010, 1(10):1063-1073.
Antonio et al, "Investigations of survivin: the past, present and future," Frontiers in Bioscience, Jan. 2011, 16(1):952-961.
Dejmek et al., "Wnt-5a/Ca2+-induced NFAT activity is counteracted by Wnt-5a/Yes-Cdc42-casein kinase 1alpha signaling in human mammary epithelial cells," Molecular and Cellular Biology, 2006, 26(16):6024-6236.
Finn et al, "Dasatinib as a Single Agent in Triple-Negative Breast Cancer: Results of an Open-Label Phase 2 Study," Clinical Cancer Research, Nov. 2011, 17(21):6905-6913.
Fornier et al., "A phase I study of dasatinib and weekly paclitaxel for metastatic breast cancer," Annals of Oncology: Official Journal of the European Society for Medical Oncology/ESMO, Dec. 2011, 22(12):2575-2581.
Hagn F. et al, "BclxL Changes Conformation upon Binding to Wild-type but Not Mutant p53 DNA Binding Domain", Journal of Biological Chemistry, vol. 285, No. 5, Jan. 29, 2010 (Jan. 29, 2010), pp. 3439-3450.
Huang et al., "Identification of candidate molecular markers predicting sensitivity in solid tumors to dasatinib: Rationale for patient selection," Cancer Research, American Association for Cancer Research, Mar. 2007, 67(5):2226-2238.
Konecny et al., "Activity of the multikinase inhibitor dasatinib against ovarian cancer cells," British Journal of Cancer, 2009, 101(10):1699-1708.
Lee et al., "Identification of Genes Involved in Liver Cancer Cell Growth Using an Antisense Library of Phage Genomic DNA," Cancer Research and Treatment, Aug. 2004, 36(4):246-254.
Luu et al., "Wnt/beta-catenin signaling pathway as a novel cancer drug targets," Current Cancer Drug Targets, Dec. 2004, 4(8):653-671.

(Continued)

*Primary Examiner* — Alicia L Otton
(74) *Attorney, Agent, or Firm* — Mueting Raasch Group

(57) ABSTRACT

The present invention provides methods of treating a subject having a Wnt/beta-catenin active cancer by administering to said subject a compound that inhibits the expression or activity of YES1, BIRC5 or BCL2L1, a compound that inhibits YAP1-beta-catenin complex formation, a compound that inhibits YAP1-beta-catenin complex binding to DNA, a compound that inhibits YAP1-beta-catenin-TBX5 complex formation, or any combination thereof. The compound can be, for example, a nucleic acid, a peptide, an antibody or a small molecule. Methods of screening for therapeutic targets for treating cancer are included.

14 Claims, 18 Drawing Sheets
Specification includes a Sequence Listing.

(56) References Cited

OTHER PUBLICATIONS

Piiper et al., "Cholecystokinin stimulates extracellular signal-regulated kinase through activation of the epidermal growth factor receptor, Yes, and protein kinase C," Journal Biol Chemistry, 2003, 278(9):7065-7072.
Ren et al., "Structural analysis of the cancer-specific promoter in mesothelin and in other genes overexpressed in cancers," The Journal of Biological Chemistry, Apr. 2011, 286(14):11960-11969.
Rosenbluh et al., "β-Catenin-driven cancers require a YAP1 transcriptional complex for survival and tumorigenesis," Cell, Dec. 2012, 151(7):1457-1473.
Stein et al., "Impact of mutant β-catenin on ABCB1 expression and therapy response in colon cancer cells," British Journal of Cancer, 2012, 106(8):1395-1405.
Xu et al., "Growth inhibition effect of [beta]-catenin small interfering RNA-mediated gene silencing on human colon carcinoma HT-29 cells," Cancer Biotherapy and Radiopharmaceuticals, Oct. 2010, 25(5):529-537.
Yu et al., "Epigenetic inactivation of T-box transcription factor 5, a novel tumor suppressor gene, is associated with colon cancer," Oncogene, Dec. 2010, 29(49):6464-6474.
Yu et al., "Once-daily Dasatinib: Expansion of Phase II Study Evaluating Safety and Efficacy of Dasatinib in Patients With Metastatic Castration-resistant Prostate Cancer," Urology, May 2011, 77(5):1166-1171.
PCT International Preliminary Report on Patentability in Appl. No. PCT/US2013/030889, dated Oct. 1, 2014, 10 pages.
PCT International Search Report and Written Opinion in Appl. No. PCT/US2013/030889, dated Jun. 2, 2013, 15 pages.
U.S. Appl. No. 14/389,310, U.S. Pat. No. 10,426,774, filed Sep. 29, 2014, William C. Hahn.
Alarcn C, Zaromytidou AI, Xi Q, Gao S, Yu J, Fujisawa S, Barlas A, Miller AN, Manova-Todorova K, Macias MJ, Sapkota G. Nuclear CDKs drive Smad transcriptional activation and turnover in BMP and TGF—pathways. Cell. Nov. 1, 20093; 1394:757-69.
Benjamini Y, Hochberg Y. Controlling the false discovery rate: a practical and powerful approach to multiple testing. Journal of the Royal statistical society: series B Methodological. Jan. 1995; 571:289-300.
Cheesman SE, Neal JT, Mittge E, Seredick BM, Guillemin K. Epithelial cell proliferation in the developing zebrafish intestine is regulated by the Wnt pathway and microbial signaling via Myd88. Proceedings of the National Academy of Sciences. Mar. 1, 20115;108(supplement_1):4570-7.
Cheung CH, Cheng L, Chang KY, Chen HH, Chang JY. Investigations of survivin: the past, present and future. Front Biosci. Jan. 1, 2011;16(3):952-61.
Fuerer C, Habib SJ, Nusse R. A study on the interactions between heparan sulfate proteoglycans and Wnt proteins. Developmental dynamics: an official publication of the American Association of Anatomists. Jan. 2010;239(1): 184-90.

He A, Kong SW, Ma Q, Pu WT. Co-occupancy by multiple cardiac transcription factors identifies transcriptional enhancers active in heart. Proceedings of the National Academy of Sciences. Apr. 5, 2011;108(14):5632-7.
Jopling C, den Hertog J. Essential role for Csk upstream of Fyn and Yes in zebrafish gastrulation. Mechanisms of development. Feb. 1, 2007;124(2):129-36.
Komuro A, Nagai M, Navin NE, Sudol M. Ww domain-containing protein YAP associates with ErbB-4 and acts as a co-transcriptional activator for the carboxyl-terminal fragment of ErbB-4 that translocates to the nucleus. Journal of Biological Chemistry. Aug. 2, 20039;278(35):33334-41.
Levy D, Adamovich Y, Reuven N, Shaul Y. Yap1 phosphorylation by c-Abl is a critical step in selective activation of proapoptotic genes in response to DNA damage. Molecular cell. Feb. 1, 20085;29(3):350-61.
Mariotti A, Kedeshian PA, Dans M, Curatola AM, Gagnoux-Palacios L, Giancotti Fg. Egf-R signaling through Fyn kinase disrupts the function of integrin a64 at hemidesmosomes: role in epithelial cell migration and carcinoma invasion. The Journal of cell biology. Oct. 2, 20019; 155(3):447-58.
Moffat J, Grueneberg DA, Yang X, Kim SY, Kloepfer AM, Hinkle G, Piqani B, Eisenhaure TM, Luo B, Grenier JK, Carpenter AE. A lentiviral RNAi library for human and mouse genes applied to an arrayed viral high-content screen. Cell. Mar. 2, 20064;124(6): 1283-98.
Mudumana SP, Wan H, Singh M, Korzh V, Gong Z. Expression analyses of zebrafish transferrin, ifabp, and elastaseB mRNAs as differentiation markers for the three major endodermal organs: liver, intestine, and exocrine pancreas. Developmental dynamics: an official publication of the American Association of Anatomists. May 2004;230(1): 165-73.
Ootani A, Li X, Sangiorgi E, Ho QT, Ueno H, Toda S, Sugihara H, Fujimoto K, Weissman IL, Capecchi MR, Kuo CJ. Sustained in vitro intestinal epithelial culture within a Wnt-dependent stem cell niche. Nature medicine. Jun. 2009; 15 (6):701-6.
Skouloudaki K, Puetz M, Simons M, Courbard JR, Boehlke C, Hartleben B, Engel C, Moeller MJ, Englert C, Bollig F, Schäfer T. Scribble participates in Hippo signaling and is required for normal zebrafish pronephros development. Proceedings of the National Academy of Sciences. May 2, 20096; 106(21):8579-84.
Sullivan-Brown J, Bisher ME, Burdine RD. Embedding, serial sectioning and staining of zebrafish embryos using JB-4 resin. Nature protocols. Jan. 2011;6(1):46-55.
Yang X, Boehm JS, Yang X, Salehi-Ashtiani K, Hao T, Shen Y, Lubonja R, Thomas SR, Alkan O, Bhimdi T, Green Tm. A public genome-scale lentiviral expression library of human ORFs. Nature methods. Aug. 2011; 8(8): 659-61.
Zhang Y, Liu T, Meyer CA, Eeckhoute J, Johnson DS, Bernstein BE, Nusbaum C, Myers RM, Brown M, Li W, Liu XS. Model-based analysis of ChIP-Seq (MACS). Genome biology. Nov. 2008; 9: 1-9.
Zhao B, Wei X, Li W, Udan RS, Yang Q, Kim J, Xie J, Ikenoue T, Yu J, Li L, Zheng P. Inactivation of YAP oncoprotein by the Hippo pathway is involved in cell contact inhibition and tissue growth control. Genes & development. Nov. 1, 2007;21(21):2747-61.

\* cited by examiner

METHODS OF TREATING CANCER HAVING AN ACTIVE Wnt/β-CATENIN PATHWAY

RELATED APPLICATIONS

This application is division of application Ser. No. 14/389,310, filed Sep. 29, 2014, which is a national stage application, filed under 35 U.S.C. § 371, of PCT/US2013/030889, filed on Mar. 13, 2013, which claims the benefit of U.S. Provisional Application No 61/618,027, filed on Mar. 30, 2012, the contents of each of which are incorporated by reference herein in their entireties.

GOVERNMENT INTEREST

This application is a divisional application of U.S. application Ser. No. 14/389,310, filed Sep. 29, 2014, now U.S. Pat. No. 10,426,774, which is a national stage application, filed under 35 U.S.C § 371, of PCT/US2013/030889, filed on Mar. 13, 2013, which claims the benefit of U.S. Provisional Application No. 61/618,027, filed on Mar. 30, 2012, the contents of each of which are incorporated by reference herein in their entireties.

FIELD OF THE INVENTION

The present invention relates generally treating cancer. Also included are methods of identifying therapeutic targets for the treatment of cancer.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: DFCI-064D01US_SeqList.txt, date recorded: Aug. 23, 2019, file size 873 bytes).

BACKGROUND OF THE INVENTION

The Wnt/β-catenin pathway has been shown to be involved in transformation and tumor maintenances of many types of cancers. Genetic experiments and mouse modeling have suggested that targeted therapies against the Wnt/β-catenin pathway could benefit patients harboring Wnt/β-catenin activating mutations. However, targeting this pathway has proven to be challenging. The prevailing view of Wnt/β-catenin signaling has been that Wnt stimulation results in stabilization and nuclear localization of β-catenin, which can then bind to transcription factors such as TCF4 and drive transcription of target genes. Although TCF4 has been postulated to be required for the transformative properties of β-catenin, recent observations have brought this notion into question. First, siRNAs targeting TCF4 caused a dramatic increase in the activity of the β-catenin/TCF4 reporter. Second, the APC$^{min}$ mouse that normally develops small intestinal tumors developed large colon tumors when crossed to a mouce lacking one allele of TCF4. Third, whole genome sequencing of 10 colon cancers showed a translocation between TCF4 and VTI1A that results in the expression of a dominant negative TCF4. Surprisingly, cell lines derived from tumors that have this translocation were dependent on it for anchorage independent growth. Fourth, analysis of copy number variation across many types of cancers showed a focal deletion of TCF4 in colorectal cancers. All of these results suggest that TCF4 might not be the sole contributor for β-catenin dependent cancers.

Thus, a need exists for the identification of therapeutic compounds useful in treating β-catenin dependent cancers.

SUMMARY OF THE INVENTION

The invention features methods of treating a subject having a Wnt/β-catenin active cancer by administering to said subject compound that inhibits the expression or activity of YES1, BIRC5 or BCL2L1, a compound that inhbits YAP1-beta-catenin complex formation, a compound that inhbits YAP1-beta-catenin complex binding to DNA, a compound that inhibits YAP1-beta-catenin-TBX5 complex formation, or any combination thereof.

The cancer is colon cancer, breast cancer, lung cancer, leukemia, prostate cancer, skin cancer, liver cancer, breast cancer, ovarian cancer, brain cancer and parthyroid cancer.

The compound is a nucleic acid, a peptide, an antibody or a small molecule. For example the compound is a YES1 inhibitor such as for example, dasatinib.

Optionally, a chemotherapeutic agent is administered to the subject.

Also provided by the invention are methods of screening for therapeutic targets for treating cancer such as a Wnt/β-catenin active cancer by providing a cell that has a Wnt/β-catenin activating mutation contacting the cell with a library of RNAi; and identifying an RNAi which is lethal to said cell.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

(A) The indicated cell lines were infected with TBX5-targeting shRNAs or with control LacZ shRNA and were subjected to quantitative RT-PCR analysis using TBX5-specific primers. (B) Proliferation and anchorage independent growth (C) of cell lines in (A). (D) 293T cells were transfected with the indicated plasmids and following FLAG IP the membrane was blotted with an HA antibody. (E) Lysates from DLD1 cells stably expressing a FLAG tagged TBX5 protein were incubated with a FLAG antibody and following blotting the membrane was stained with the indicated antibodies. (F and G) HuTu80 cells infected with TBX5 specific shRNAs were incubated with β-catenin (F) or YAP1 (G) antibodies and following immunoprecipitation the abundance of BCL2L1 or BIRC5 DNA was measured using PCR analysis. (H) mRNA levels of BC2L1 and BIRC5 in HCT116 cells expressing TBX5-specific shRNAs.

Figure 10:
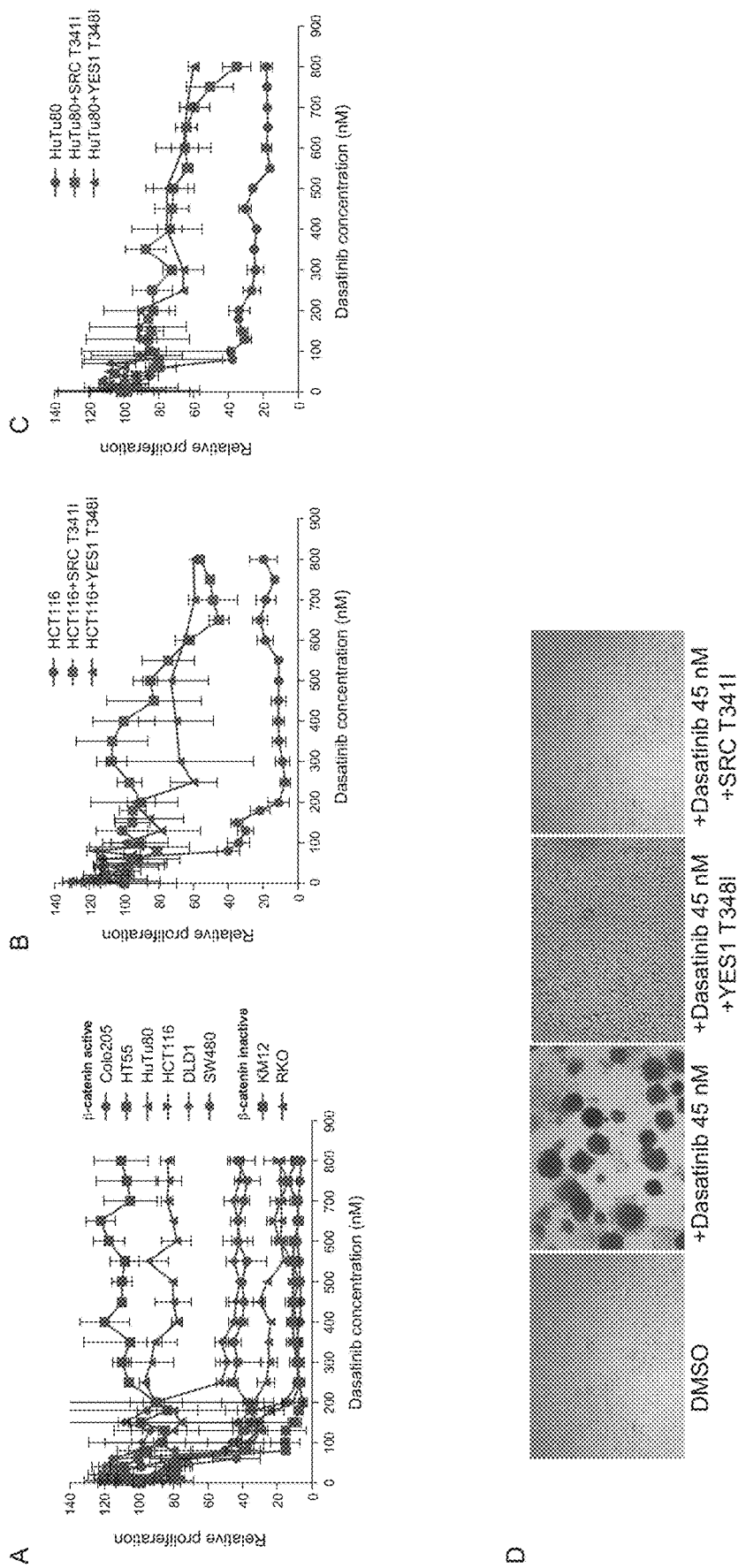

FIG. 10: Dasatinib treatment impairs the proliferation of Wnt/β-catenin active cell lines by inhibiting SRC family members. (A) The indicated cancer cell lines were treated with various concentrations of dasatinib and proliferation was measured 7 days post treatment. (B) HCT116 or (C) HuTu80 cells stably expressing a dastinib resistant YES1 (T3481) or SRC (T3411) were treated as in (A). (D) Representative picture of HCT116 cells treated as in (B).

Figure 11:
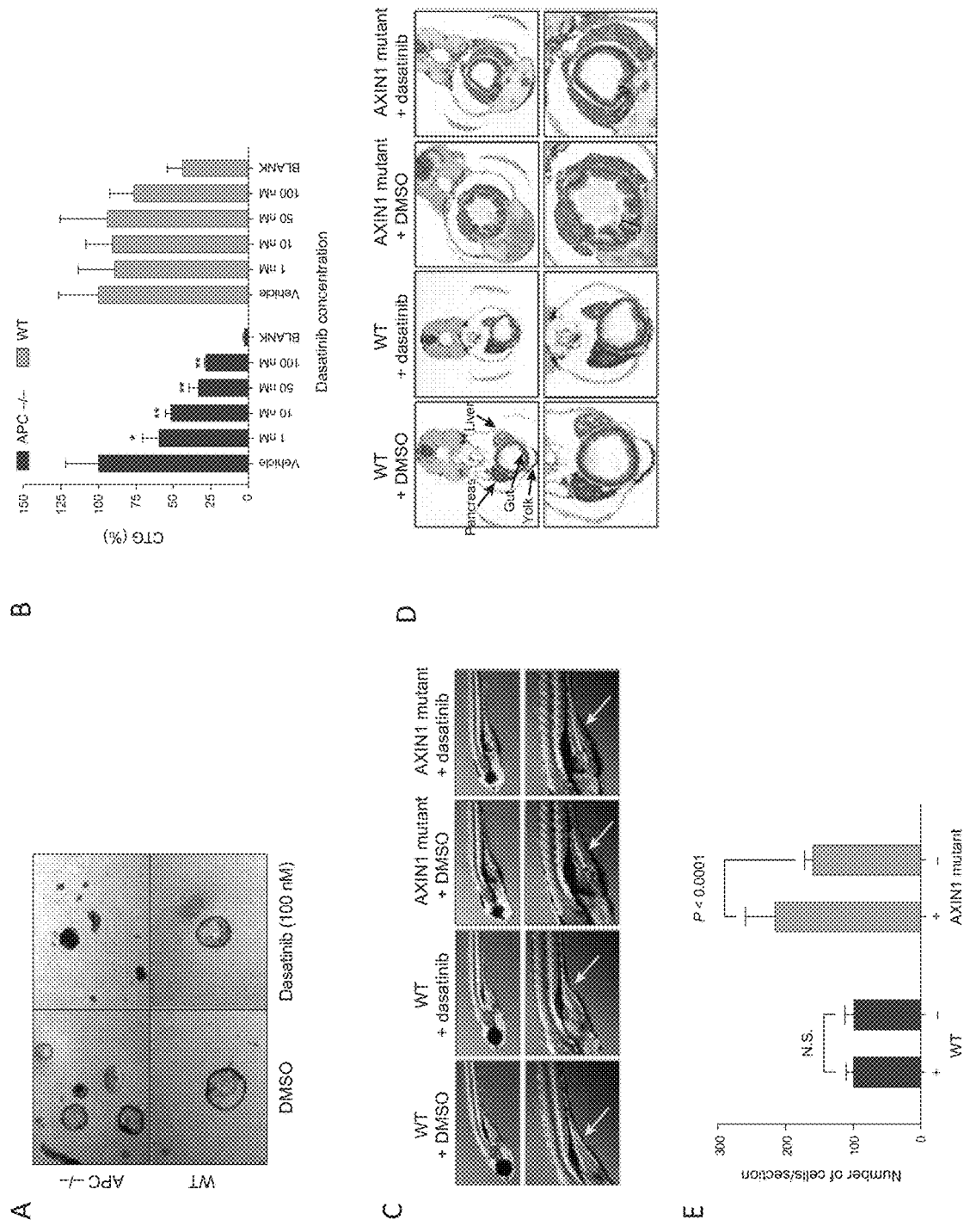

FIG. 11: Dasatinib treatment impairs the proliferation of β-catenin active cell lines. (A) Representative images of colon organoids derived from WT or APC null mice treated for 6 days with 100 nM of dasatinib. (B) Quantification of results in (A). Error bars represent SD from four replicates. Blank denotes wells where no organoids were added. (C) WT or AXIN1 mutant (Masterblind) zebrafish were treated with 2 μM of dasatinib from 6-8 dpf. Arrow indicates developing gut. (D) H&E staining of zebrafish in (C) width of epithelium is noted by bars. (E) The number of epithelial cells/section was measured in WT or AXIN1 mutant zebrafish treated with 2 μM of dasatinib or DMSO. Error bars represent the SD from 20 different sections from five treated fish. p value was calculated by using Student's t test.

Figure 12:
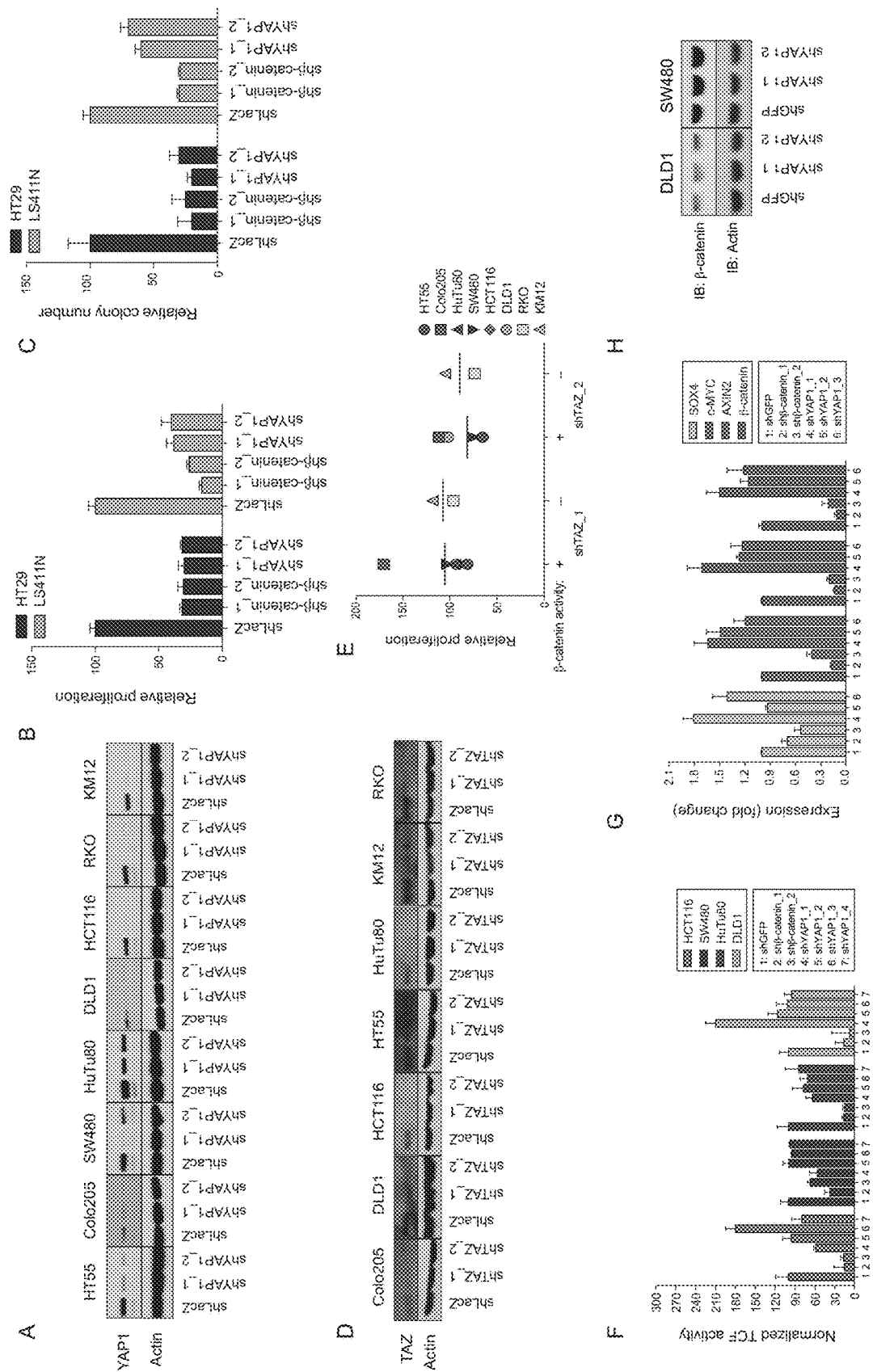

FIG. 12: Suppression of YAP1 does not effect β-catenin/TCF4 signaling. (A) YAP1 protein levels 4 days post infection with YAP1 targeting shRNAs. (B) Proliferation and (C) Anchorage independent growth of HT29 and LSN411N cells following YAP1 or β-catenin knockdown. (D) TAZ protein levels 4 days post infection with TAZ targeting shRNAs. (E) Proliferation of cells in (D). (F) β-catenin/TCF4 reporter activity was measured 5 days post infection with β-catenin or YAP1 targeting shRNAs. (G) Quantitative PCR analysis of cells in (F). (H) β-catenin levels were measured in the indicated cell lines 4 days post infection with YAP1 targeting shRNAs.

Figure 13:
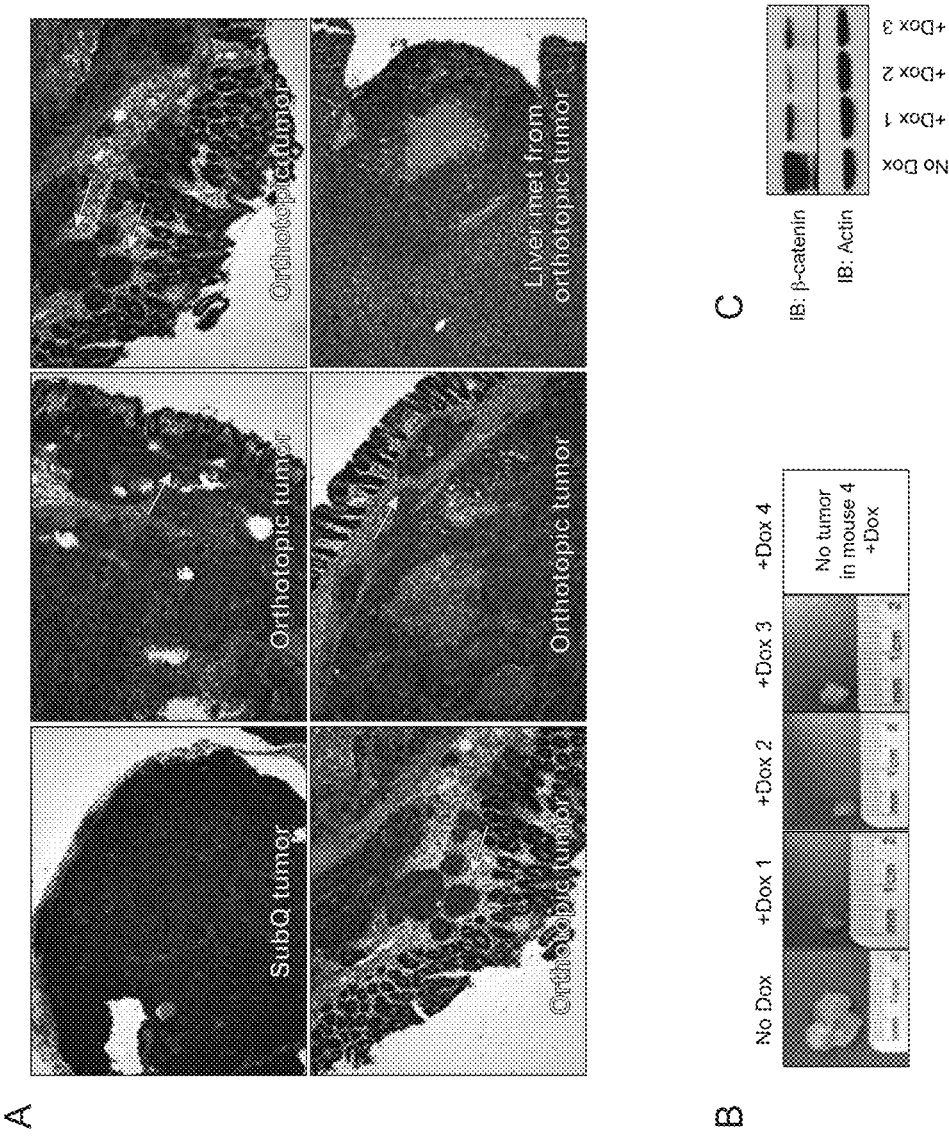

FIG. 13: Orthotopic model of colon cancer. (A) H&E staining of subqutenious or orthotopic colon tumors derived from the HCT116 cell line. (B) Orthotopic colon tumors containing a doxycycline inducible β-catenin shRNA were treated with doxycycline 48 hours post orthotopic implementation. Tumors were extracted 3 weeks post implementation. (C) Immunoblot analysis of tumors in (B).

Figure 14:
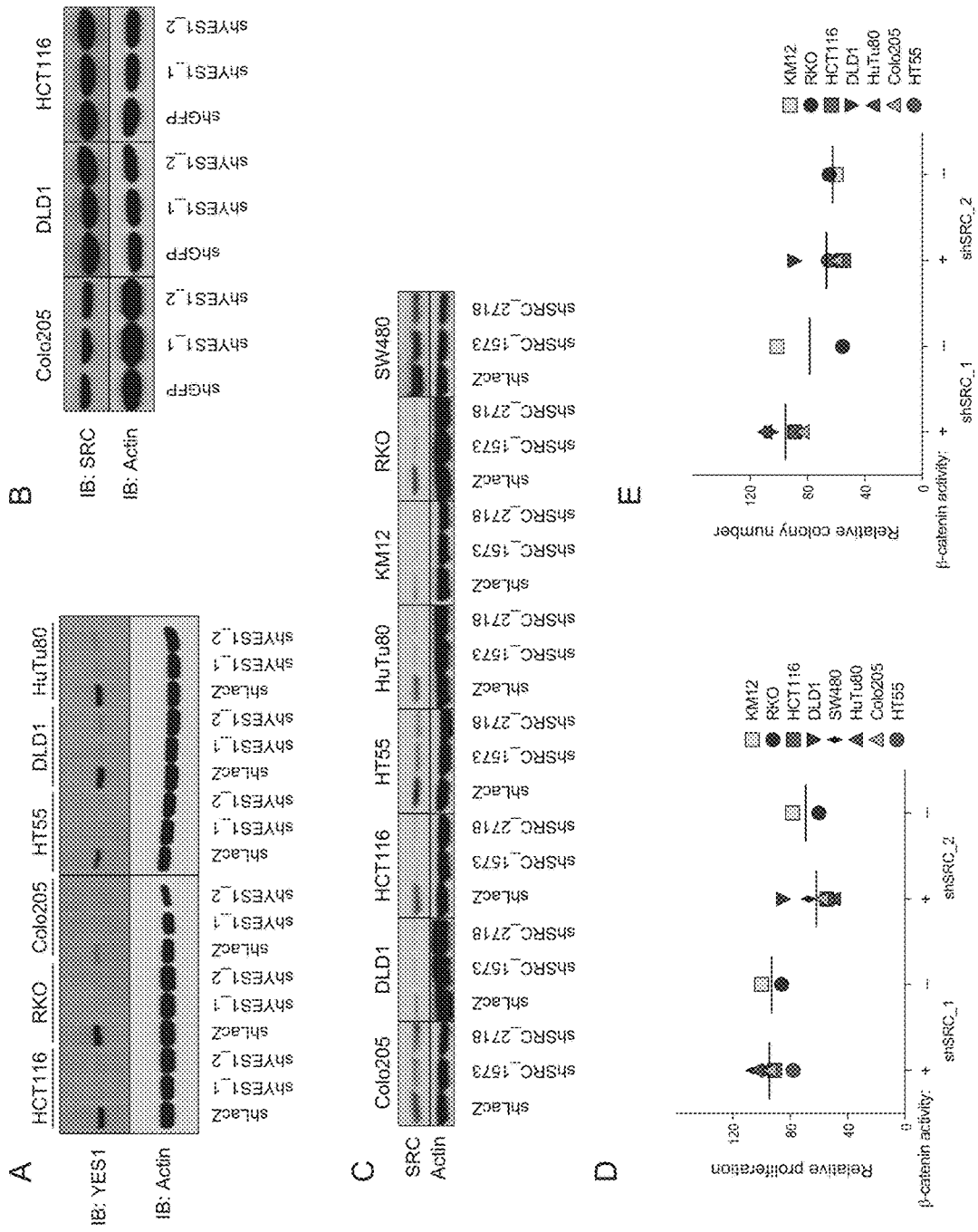

FIG. 14: SRC knockdown does not affect Wnt/β-catenin active cancers. (A) YES1 protein levels 4 days post infection with YES1 targeting shRNAs. (B) Expression of SRC following knockdown of YES1. (C) SRC protein levels 4 days post infection with SRC targeting shRNAs. (D) Proliferation or (E) Anchorage independent growth of the indicated cell lines following SRC knockdown.

Figure 15:
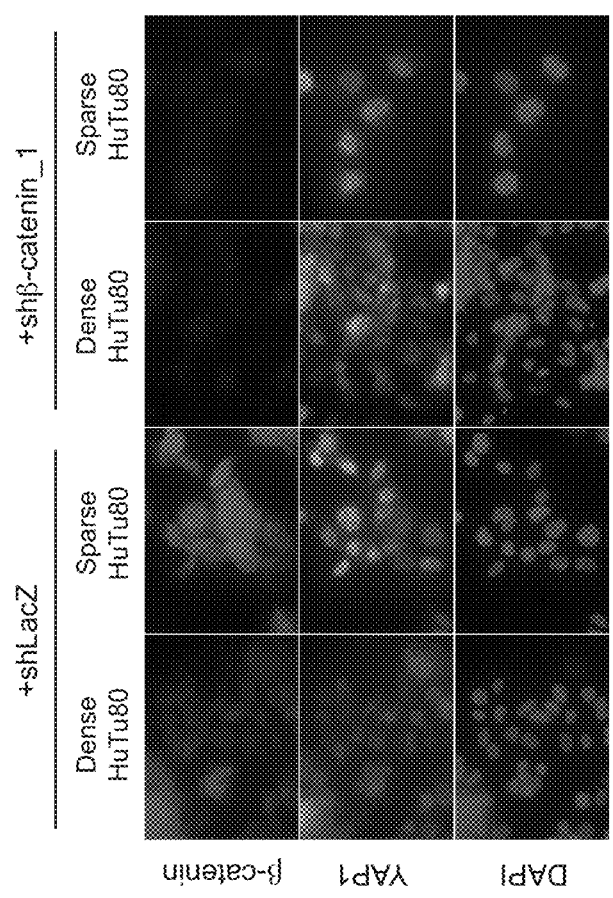

FIG. 15: Nuclear YAP1 is present in all colon cancer cell lines independent of Wnt/β-catenin pathway activity. HuTu80 cell line was infected with a β-catenin specific or LacZ control shRNA and following sparse or dense plating were stained for β-catenin or YAP1.

Figure 16:
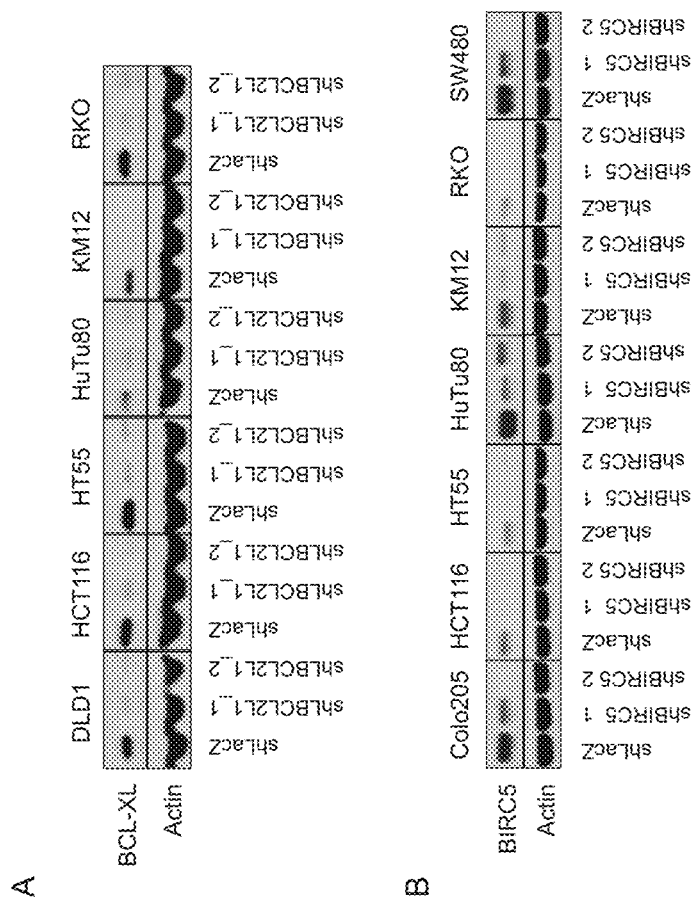

FIG. 16: shRNAs targeting BCL2L1 and BIRC5. (A) BCL-XL or (B) BIRC5 protein levels 4 days post infection with specific targeting shRNAs.

Figure 17:
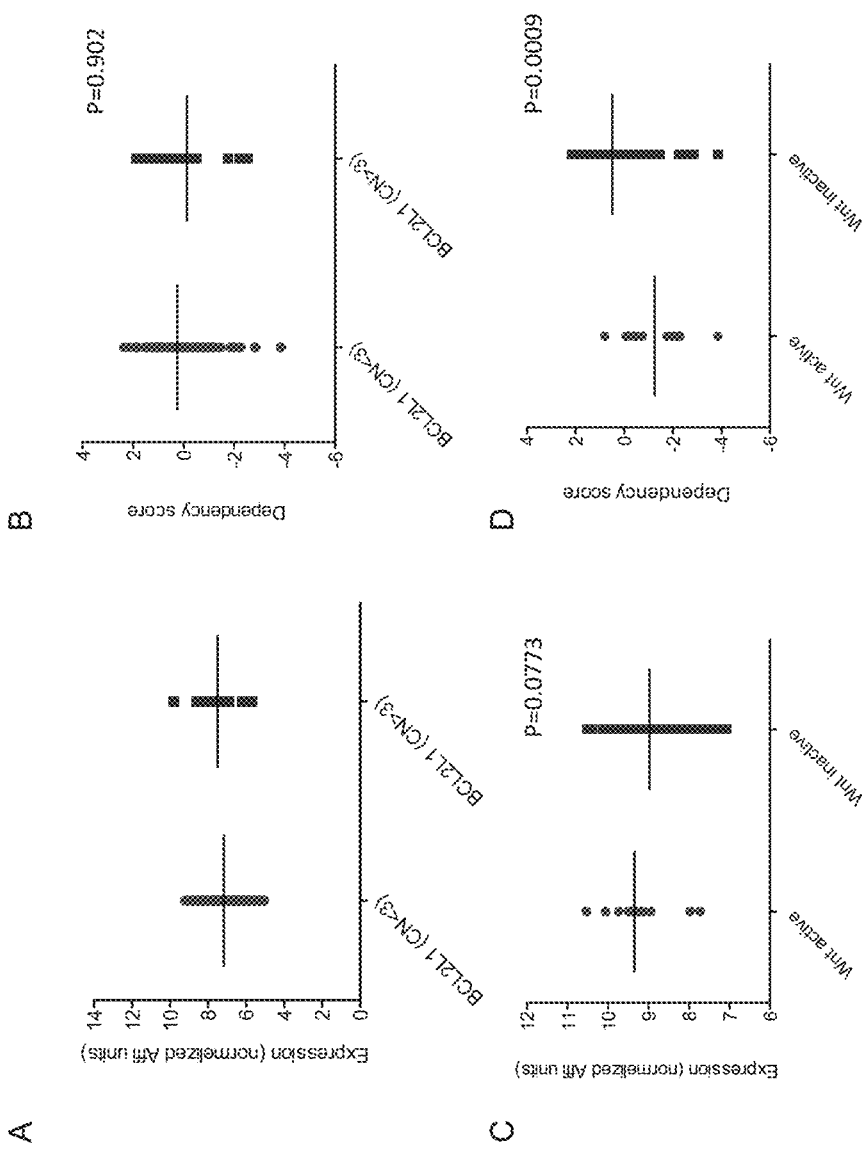

FIG. 17: Wnt/β-catenin activity and not amplification of BCL2L1 predicts BCL2L1 expression and dependency. (A) Expression of BCL2L1 in amplified vs. non-amplified cell lines. (B) BCL2L1 dependency scores in amplified vs. non-amplified cell lines. (C) Expression of BCL2L1 in Wnt/β-catenin active vs. non-active cell lines. (D) BCL2L1 dependency scores in Wnt/β-catenin active vs. non-active cell lines. BCL2L1 expression and copy number variation data were obtained from the CCLE database.

Figure 18:
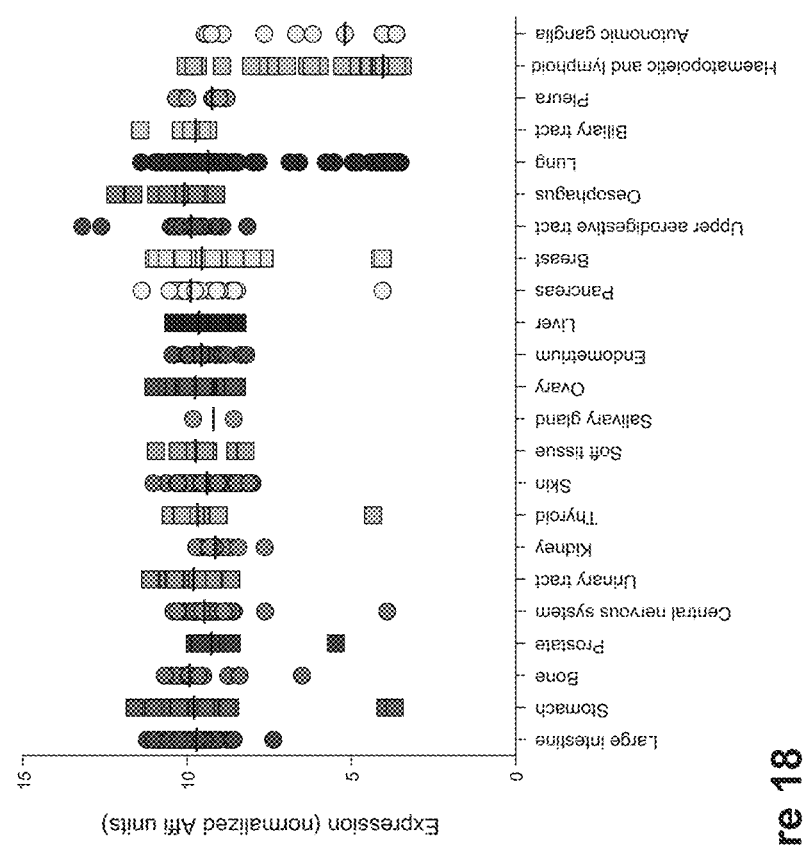

FIG. 18: Expression of YAP1 across CCLE cell lines. YAP1 expression across 807 cancer cell lines.

DETAILED DESCRIPTION OF THE INVENTION

The invention is based in part upon the surprising discovery that genes that regulate YAP1 are essential for the survival of Wnt/β-catenin active cancers. More importantly, it was also discovered that the kinase YES1 regulates YAP1 and is also essential for the proliferation of Wnt and beta-catenin active cancers. Accordingly, targeting YES1 and YAP1 and their targets may be useful in treating Wnt/beta-catenin driven cancers.

The Wnt/β-catenin pathway has been shown to be involved in transformation and tumor maintenances of many types of cancers. Although TCF4 has been believed to be required for the transformative properties of β-catenin, recent observations have brought this notion into question, suggesting that TCF4 might not be the sole contributor for β-catenin dependent cancers. Using colon cancer cell lines we were able to show that suppression of TCF4 did not inhibit the β-catenin/TCF4 reporter activity and was only partially able to reduce the proliferation and anchorage independent growth of β-catenin dependent cancers. Thus, we concluded that TCF4 could only partially explain the dependency of Wnt/β-catenin activated cancers on β-catenin and hypothesized that other pathways might synergize with β-catenin to promote transformation.

To find genes that are required for the proliferation of Wnt/β-catenin activated cancers we used an unbiased loss of function screen. Using pooled shRNA screens we were able to screen a large panel of 85 cancer cell lines and detect genes that their expression is essential for the proliferation/viability of Wnt/β-catenin active cancers. The use of large number of cell lines allowed us to perform meaningful statistical analysis and to determine the significance in which a gene distinguishes two groups (i.e., Wnt/β-catenin active cancers compared to Wnt/β-catenin inactive ancers). Indeed, when classifying cells randomly we could not detect any gene that significantly distinguished the two random groups indicating that scoring genes truly distinguish groups of interest. The reliability of the pooled shRNA screen is further exemplified by the fact that when we classified cell lines based on the mutational status of known oncogenes the expected oncogene showed up as the number one hit distinguishing the two groups.

Classification of cancer cell lines by the status of the Wnt/β-catenin pathway revealed 50 genes that could significantly distinguish the two groups. To our surprise, only two of these genes, β-catenin itself and BCL9L could inhibit the β-catenin/TCF4 reporter activity. This result suggests that besides the TCF4-β-catenin complex there are other cellular components that contribute to the cancer phenotype associated with β-catenin.

Along with β-catenin we detected 49 other genes that are required for the proliferation of Wnt/β-catenin activated cancers. Of these we found a striking enrichment for genes that are regulated by YAP1. YAP1 has been reported to be regulated by the Hippo pathway and by phosphorylation of tyrosine kinases such as YES1. Our results show that YAP1 is essential for the proliferation and maintenances of Wnt/β-catenin activated cancers.

We provide a clear understanding of the involvement of YAP1 in β-catenin dependent cancers. We show that YAP1 expression is specifically important for the survival of Wnt/β-catenin dependent cancers. However, we show that colon cancer cell lines that do not exhibit Wnt/β-catenin activity such as RKO and KM12 do not require YAP1 for their survival even though they have nuclear YAP1. Using the β-catenin/TCF4 reporter we show that YAP1 depletion did not affect β-catenin/TCF4 reporter activity. Moreover, two colon cancer cell lines (HT29 and LS411N) that have APC mutations and are sensitive to β-catenin knockdown were also sensitive to YAP1 knockdown but did not show β-catenin/TCF4 reporter activity. Thus, we show that YAP1 is important for β-catenin driven cancers and that this is in a mechanism that is distinct from the TCF4/β-catenin pathway. Importantly, we show that YAP1 sensitivity is not unique to the colon lineage but to oncogenic addiction to β-catenin.

Our results suggest that YAP1 induces transformation by cooperating with β-catenin that is the limiting factor in these cancers. This is implied from our results showing that immortalized cell lines such as HA1EM need YAP1 to enable β-catenin induced transformation. Similar to β-catenin when stabilized YAP1 was introduced into HA1EM it was able to promote anchorage independent growth of these cells. A similar proliferation phenotype was observed in mouse models that stabilized YAP1 by inactivating the Hippo pathway or by expression of a mutated YAP1. However, although forced expression of YAP1 could promote this growth phenotype, sequencing projects have not detected any of these mutations in human cancers. Furthermore we could not detect any up-regulation of YAP1 expression in a panel of 807 cancer cell lines (FIG. 18). Thus, we conclude that although forced expression of YAP1 could promote a similar phenotype to that of β-catenin the levels of β-catenin are the limiting factor in human cancer.

Our results suggest that components that could regulate the Hippo pathway are involved in Wnt/β-catenin induced transformation however; we could not see any correlation between the Hippo pathway activity and YAP1 or β-catenin sensitivity. We show that expression of the anti-apoptotic genes BIRC5 and BCL2L1 is dependent on the YAP1(3-catenin complex. These observations are further supported by CHIP sequencing experiments showing that YAP1 could bind to the promoter region of both BIRC5 and BCL2L1. CHIP-Seq data using β-catenin specific antibodies showed that also β-catenin could bind to these regions. A further indication for the involvement of BCL2L1 in the β-catenin-YAP1 induced transformation could be inferred from mouse models of stabilized YAP1. Camargo et al. showed that forced expression of stabilized YAP1 promotes the expression of BCL2L1 specifically in the colon and not in ES cells. This is in agreement with our findings since β-catenin has been well characterized to be activated in the stem cell compartment of the colon. When overexpressed both YES1 and SRC were able to promote tyrosine phosphorylation of YAP1. However, we observed that suppression of YES1 expression abrogated the interaction between YAP1 and β-catenin indicating that YES1 is responsible for this interaction in colon cancers. Interestingly the same tyrosine on YAP1 is phosphorylated by the kinase Abl in response to DNA stress and results in the expression of pro-apoptotic genes. This dual function of YAP1 may represent another layer of regulation that is dependent on the presence of specific kinases and could suggest that YES1 has other functions in regulation of this interaction.

Targeting of β-catenin dependent cancers has proven to be challenging. Our results demonstrate that the YAP1(3-catenin-TBX5 complex is one of the major drivers of β-catenin induced transformation. The YAP1-β-catenin-TBX5 complex was found play a role in the transcription of cell survival factors BIRC5 and BCL2L1 in cancer cell lines, thereby indicating that this complex plays a critical role in the tumorgenicity of Wnt/β-catenin active cancers. Knockdown of YAP1 in immortalized cells did not affect their proliferation indicating that YAP1 may be a cancer specific target of β-catenin derived tumors. We further show that the SRC family members are involved in regulating this interaction and that small molecule inhibitors could inhibit the growth of these tumors by inhibiting the formation of this complex. New small molecule inhibitors of BCL2L1 and BIRC5 are currently being tested and may also prove to be useful for targeting of Wnt/β-catenin active cancers.

In conclusion, our data suggests that in β-catenin derived cancers phosphorylation of YAP1 by YES1 promotes the DNA binding of the YAP1-β-catenin-TBX5 complex formation. This complex could bind to DNA and drive the expression of anti apoptotic genes, for example BCL2L1 and BIRC5, that are essential for the cancer phenotype associated with β-catenin.

Accordingly, these results indicate that, therapy with a YES1 inhibitor; an inhibitor of the YAP1-β-catenin-TBX5 transcription complex, and inhibitors of BIRC5 and BCL2L1 provides therapeutic benefits in Wnt/β-catenin active cancers such as colon cancer, breast cancer, lung cancer, leukemia, prostate cancer, skin cancer including melanoma, liver cancer, breast cancer, ovarian cancer, brain cancers including glioblastomas's and meningioma's and parthyroid cancer.

Yamaguchi sarcoma viral oncogene homolog 1 (YES1) is the cellular homolog of the Yamaguchi sarcoma virus oncogene. The encoded protein has tyrosine kinase activity and belongs to the src family of proteins. This gene lies in close proximity to thymidylate synthase gene on chromosome 18, and a corresponding pseudogene has been found on chromosome 22.

A YES 1 inhibitor is a compound that decreases expression or activity of YES1. A decrease in YES1 expression or activity is defined by a reduction of a biological function of the tyrosine kinase. A tyrosine kinase biological function includes for example, catalyzing the phosphorylation of tyrosine.

YES1 kinase activity is measured by detecting phosphorylation of a protein. YES1 inhibitors are known in the art or are identified using methods described herein. For example, a YES1 inhibitor is identified by detecting a decrease the tyrosine kinase mediated transfer phosphate from ATP to protein tyrosine residues.

The YES1 inhibitor inhibits the phosphorylation of YAP1 either specifically of non-specifically.

The YES1 inhibitor can be a small molecule. A "small molecule" as used herein, is meant to refer to a composition that has a molecular weight in the range of less than about 5 kD to 50 daltons, for example less than about 4 kD, less than about 3.5 kD, less than about 3 kD, less than about 2.5 kD, less than about 2 kD, less than about 1.5 kD, less than about 1 kD, less than 750 daltons, less than 500 daltons, less than about 450 daltons, less than about 400 daltons, less than about 350 daltons, less than about 300 daltons, less than 250 daltons, less than about 200 daltons, less than about 150 daltons, less than about 100 daltons. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

The YES1 inhibitor is an antibody or fragment thereof specific for YES1.

Alternatively, the YES1 inhibitor is for example an antisense YES1 nucleic acid, a YES1-specific short-interfering RNA, or a YES1-specific ribozyme. By the term "siRNA" is meant a double stranded RNA molecule which prevents translation of a target mRNA. Standard techniques of introducing siRNA into a cell are used, including those in which DNA is a template from which an siRNA RNA is transcribed. The siRNA includes a sense YES1 nucleic acid sequence, an anti-sense YES1 nucleic acid sequence or both. Optionally, the siRNA is constructed such that a single transcript has both the sense and complementary antisense sequences from the target gene, e.g., a hairpin.

Binding of the siRNA to a YES1 transcript in the target cell results in a reduction in YES1 production by the cell. The length of the oligonucleotide is at least 10 nucleotides and may be as long as the naturally-occurring YES1 transcript. Preferably, the oligonucleotide is 19-25 nucleotides in length. Most preferably, the oligonucleotide is less than 75, 50, 25 nucleotides in length.

The YES 1 inhibitor is for example dasatinib, mimetics or derivatives thereof. Other YES 1 inhibitors are known in the art.

An inhibitor of the YAP1-beta-catenin interaction, i.e., YAP1-beta catenin complex formation, is a compound that decreases expression or activity of genes downstream in the pathway. For example, an inhibitor of the YAP1-beta catenin interation inhibits or decreases the expression of anti-apoptotic genes such as BIRC5 and BCL2L1.

An inhibitor of the YAP1-beta-catenin-TBX5 interaction, i.e., YAP1-beta catenin-TBX5 complex formation, is a compound that decreases expression or activity of genes downstream in the pathway. For example, an inhibitor of the YAP1-beta catenin-TBX5 complex inhibits or decreases the expression of anti-apoptotic genes such as BIRC5 and BCL2L1.

An inhibitor of the YAP1-β-catenin-TBX5 interaction can inhibit, prevent, or decrease interaction between YAP1 and β-catenin or the binding of the YAP1-β-catenin-TBX5 complex to DNA. In another embodiment, the inhibitor of the YAP1-β-catenin-TBX5 interaction can inhibit, prevent, or decrease interaction between β-catenin and TBX5. In a further embodiment, the inhibitor YAP1-β-catenin-TBX5 interaction can inhibit interaction between YAP1 and TBX5. In yet another embodiment, an inhibitor of the YAP1-β-catenin-TBX5 interaction may inhibit or prevent the complex binding to DNA, for example, at promoters of downstream genes normally regulated by the complex.

The inhibitor of the YAP1-beta catenin interaction, or the YAP1-beta catenin-TBX5 interaction can be a small molecule. A "small molecule" as used herein, is meant to refer to a composition that has a molecular weight in the range of less than about 5 kD to 50 daltons, for example less than about 4 kD, less than about 3.5 kD, less than about 3 kD, less than about 2.5 kD, less than about 2 kD, less than about 1.5 kD, less than about 1 kD, less than 750 daltons, less than 500 daltons, less than about 450 daltons, less than about 400 daltons, less than about 350 daltons, less than about 300 daltons, less than 250 daltons, less than about 200 daltons, less than about 150 daltons, less than about 100 daltons. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

The YAP1 inhibitor is an antibody or fragment thereof specific for YAP1 or beta-catenin.

Alternatively, the YAP1 inhibitor is for example an antisense YAP1 nucleic acid, a YAP1-specific short-interfering RNA, or a YAP1-specific ribozyme. By the term "siRNA" is meant a double stranded RNA molecule which prevents translation of a target mRNA. Standard techniques of introducing siRNA into a cell are used, including those in which DNA is a template from which a siRNA RNA is transcribed. The siRNA includes a sense YAP1 nucleic acid sequence, an anti-sense YAHP1 nucleic acid sequence or both. Optionally, the siRNA is constructed such that a single transcript has both the sense and complementary antisense sequences from the target gene, e.g., a hairpin.

TBX5 is a member of the T-box family of transcription factors. The TBX5 inhibitor is an antibody or fragment thereof specific for TBX5.

Alternatively, the TBX5 inhibitor is for example an antisense TBX5 nucleic acid, a TBX5-specific short-interfering RNA, or a TBX5-specific ribozyme. By the term "siRNA" is meant a double stranded RNA molecule which prevents translation of a target mRNA. Standard techniques of introducing siRNA into a cell are used, including those in which DNA is a template from which a siRNA RNA is transcribed. The siRNA includes a sense TBX5 nucleic acid sequence, an anti-sense BIRC5 nucleic acid sequence or both. Optionally, the siRNA is constructed such that a single transcript has both the sense and complementary antisense sequences from the target gene, e.g., a hairpin.

Baculoviral inhibitor of apoptosis repeat-containing 5 (BIRC5) also known as survivin. BIRC5 is a member of the inhibitor of apoptosis (IAP) family. The BIRC5 protein functions to inhibit caspase activation, thereby leading to negative regulation of apoptosis or programmed cell death. This has been shown by disruption of BIRC5 induction pathways leading to increase in apoptosis and decrease in tumour growth. The BIRC5 protein is expressed highly in most human tumours and fetal tissue, but is completely absent in terminally differentiated cells. BIRC5 expression is also highly regulated by the cell cycle and is only expressed in the G2-M phase. It is known that survivin localizes to the mitotic spindle by interaction with tubulin during mitosis and may play a contributing role in regulating mitosis.

A BIRC5 inhibitor is a compound that decreases expression or activity of BIRC5. A decrease in BIRC5 expression or activity is defined by a reduction of a biological function of the apoptosis inhibitor. BIRC5 activity is measured by detecting inhibition of apoptosis. BIRC5 inhibitors are known in the art or are identified using methods described herein. For example, a BIRC5 inhibitor is identified by detecting a decrease in the inhibition of apoptosis, i.e., an increase in apoptosis in a cell. Apoptosis is measured by methods known in the art. For example, apoptois is determined by measuring DNA fragmentation, membrane phospholipid changes, or ICE-like protease activation.

The BIRC5 inhibitor can be a small molecule. A "small molecule" as used herein, is meant to refer to a composition that has a molecular weight in the range of less than about 5 kD to 50 daltons, for example less than about 4 kD, less than about 3.5 kD, less than about 3 kD, less than about 2.5 kD, less than about 2 kD, less than about 1.5 kD, less than about 1 kD, less than 750 daltons, less than 500 daltons, less than about 450 daltons, less than about 400 daltons, less than about 350 daltons, less than 300 daltons, less than 250 daltons, less than about 200 daltons, less than about 150 daltons, less than about 100 daltons. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

The BIRC5 inhibitor is an antibody or fragment thereof specific for BIRC5.

Alternatively, the BIRC5 inhibitor is for example an antisense BIRC5 nucleic acid, a BIRC5-specific short-interfering RNA, or a BIRC5-specific ribozyme. By the term "siRNA" is meant a double stranded RNA molecule which prevents translation of a target mRNA. Standard techniques of introducing siRNA into a cell are used, including those in which DNA is a template from which a siRNA RNA is transcribed. The siRNA includes a sense BIRC5 nucleic acid sequence, an anti-sense BIRC5 nucleic acid sequence or both. Optionally, the siRNA is constructed such that a single transcript has both the sense and complementary antisense sequences from the target gene, e.g., a hairpin.

Binding of the siRNA to a BIRC5 transcript in the target cell results in a reduction in BIRC5 production by the cell. The length of the oligonucleotide is at least 10 nucleotides and may be as long as the naturally-occurring BIRC5 transcript. Preferably, the oligonucleotide is 19-25 nucleotides in length. Most preferably, the oligonucleotide is less than 75, 50, 25 nucleotides in length.

The BIRC5 inhibitor is for example YM155 or derivatives thereof. Other BIRC5 inhibitors are known in the art.

Bcl-2-like protein 1 (BCL2L1) belongs to the BCL-2 protein family. BCL-2 family members form hetero- or homodimers and act as anti- or pro-apoptotic regulators that are involved in a wide variety of cellular activities. The proteins encoded by this gene are located at the outer mitochondrial membrane, and have been shown to regulate outer mitochondrial membrane channel (VDAC) opening. VDAC regulates mitochondrial membrane potential, and thus controls the production of reactive oxygen species (ROS) and release of cytochrome C by mitochondria, both of which are the potent inducers of cell apoptosis. Two alternatively spliced transcript variants, which encode distinct isoforms, have been reported. The longer isoform acts as an apoptotic inhibitor and the shorter form acts as an apoptotic activator.

A BCL2L1 inhibitor is a compound that decreases expression or activity of BCL2L1. A decrease in BCL2L1 expression or activity is defined by a reduction of a biological function of the apoptosis inhibitor. BCL2L1 activity is measured by detecting inhibition of apoptosis. BCL2L1 inhibitors are known in the art or are identified using methods described herein. For example, a BCL2L1 inhibitor is identified by detecting a decrease in the inhibition of apoptosis, i.e., an increase in apoptosis in a cell. Apoptosis is measured by methods known in the art. For example, apoptois is determined by measuring DNA fragmentation, membrane phospholipid changes, or ICE-like protease activation.

The BCL2L1 inhibitor can be a small molecule. A "small molecule" as used herein, is meant to refer to a composition that has a molecular weight in the range of less than about 5 kD to 50 daltons, for example less than about 4 kD, less than about 3.5 kD, less than about 3 kD, less than about 2.5 kD, less than about 2 kD, less than about 1.5 kD, less than about 1 kD, less than 750 daltons, less than 500 daltons, less than about 450 daltons, less than about 400 daltons, less than about 350 daltons, less than 300 daltons, less than 250 daltons, less than about 200 daltons, less than about 150 daltons, less than about 100 daltons. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

The BCL2L1 inhibitor is an antibody or fragment thereof specific for BCL2L1.

Alternatively, the BCL2L1 inhibitor is for example an antisense BCL2L1 nucleic acid, a BCL2L1-specific short-interfering RNA, or a BCL2L1-specific ribozyme. By the term "siRNA" is meant a double stranded RNA molecule which prevents translation of a target mRNA. Standard techniques of introducing siRNA into a cell are used, including those in which DNA is a template from which an siRNA RNA is transcribed. The siRNA includes a sense BCL2L1 nucleic acid sequence, an anti-sense BCL2L1 nucleic acid sequence or both. Optionally, the siRNA is constructed such that a single transcript has both the sense and complementary antisense sequences from the target gene, e.g., a hairpin.

Binding of the siRNA to a BCL2L1 transcript in the target cell results in a reduction in BIRC5 production by the cell. The length of the oligonucleotide is at least 10 nucleotides and may be as long as the naturally-occurring BCL2L1 transcript. Preferably, the oligonucleotide is 19-25 nucleotides in length. Most preferably, the oligonucleotide is less than 75, 50, 25 nucleotides in length.

The BCL2L1 inhibitor is for example ABT-263 or derivatives thereof. Other BCL2L1 inhibitors are known in the art.

Therapeutic Methods

The growth of cells is inhibited, e.g. reduced by contacting a Wnt/β-catenin active cancer cell with composition containing a YES1 inhibitor; an inhibitor of the YAP1-β-catenin interaction, and a BIRC5 inhibitor or a BCL2L1 inhibitor provides therapeutic benefits in Wnt/β-catenin active cancers. Wnt/β-catenin active cancers have a Wnt/β-catenin actrivating mutation By inhibition of cell growth is meant the cell proliferates at a lower rate or has decreased viability compared to a cell not exposed to the composition. Cell growth is measured by methods know in the art such as, the MTT cell proliferation assay or meauremnt of total GFP from GFP expresiing cell lines.

Cells are directly contacted with the compound. Alternatively, the compound is administered systemically.

The cell is a tumor cell such as a colon cancer, breast cancer, lung cancer, leukemia, prostate cancer, and parthyroid cancer or any other Wnt/β-catenin active cancer.

The methods are useful to alleviate the symptoms of a variety of cancers. Any Wnt/β-catenin active cancer is amendable to treatment by the methods of the invention. In some aspects the subject is suffering from colon cancer, breast cancer, lung cancer, leukemia, prostate cancer, or parthyroid cancer. Treatment is efficacious if the treatment leads to clinical benefit such as, a decrease in size, prevalence, or metastatic potential of the tumor in the subject. When treatment is applied prophylactically, "efficacious" means that the treatment retards or prevents tumors from forming or prevents or alleviates a symptom of clinical symptom of the tumor. Efficaciousness is determined in association with any known method for diagnosing or treating the particular tumor type.

Therapeutic Administration

The invention includes administering to a subject composition comprising a YES1 inhibitor, an inhibitor of the YAP1-β-catenin interaction, an inhibitor of the YAP1-β-catenin-TBX5 complex formation, a BIRC5 inhibitor, a BCL2L1 inhibitor or any combination thereof.

In one embodiment, the present invention includes methods further comprising administering to a subject a chemotherapeutic agent. Chemotherapeutic agents are known in the art. Chemotherapeutic agents can be, for example, but not limited to: alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitor, interferons, platinum cooridnation complexes, anthracenedione substituted urea, methyl hydrazine derivatives, adrenocortical suppressant, adrenocorticosteroides, progestins, estrogens, antiestrogen, androgens, antiandrogen, and gonadottopin-releasing hormone analog. Other chemotherapeutic agents include, but are not limited to: prednisone, fluorouracil (e.g., 5-fluorouracil (5-FU)), anastrozole, bicalutamide, carboplatin, cisplatin, chlorambucil, docetaxel, doxorubicin, etoposide, flutamide, interferon-alpha, letrozole, leuprolide, megestrol, mitomycin, paclitaxel, plicamycin, tamoxifen, thiotepa, topotecan, valrubicin, vinylastin, vincristine, and any combination of any of the foregoing.

In some aspects, the chemotherapeutic agent may be administered simultaneous to or in alternation with a composition comprising a YES1 inhibitor, an inhibitor of the YAP1-β-catenin interaction, an inhibitor of the YAP1-β-catenin-TBX5 complex formation, a BIRC5 inhibitor, a BCL2L1 inhibitor or any combination thereof.

An effective amount of a therapeutic compound is preferably from about 0.1 mg/kg to about 150 mg/kg. Effective doses vary, as recognized by those skilled in the art, depending on route of administration, excipient usage, and coadministration with other therapeutic treatments including use of other anti-proliferative agents or therapeutic agents for treating, preventing or alleviating a symptom of a cancer. A therapeutic regimen is carried out by identifying a mammal, e.g., a human patient suffering from a cancer that has a Wnt/β-catenin active cancer using standard methods. For example, the subject has a Wnt/β-catenin actrivating mutation.

The pharmaceutical compound is administered to such an individual using methods known in the art. Preferably, the compound is administered orally, rectally, nasally, topically or parenterally, e.g., subcutaneously, intraperitoneally, intramuscularly, and intravenously. The inhibitors are optionally formulated as a component of a cocktail of therapeutic drugs to treat cancers. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

The therapeutic compounds described herein are formulated into compositions for other routes of administration utilizing conventional methods. For example, the therapeutic compounds are formulated in a capsule or a tablet for oral administration. Capsules may contain any standard pharmaceutically acceptable materials such as gelatin or cellulose. Tablets may be formulated in accordance with conventional procedures by compressing mixtures of a therapeutic compound with a solid carrier and a lubricant. Examples of solid carriers include starch and sugar bentonite. The compound is administered in the form of a hard shell tablet or a capsule containing a binder, e.g., lactose or mannitol, conventional filler, and a tableting agent. Other formulations include an ointment, suppository, paste, spray, patch, cream, gel, resorbable sponge, or foam. Such formulations are produced using methods well known in the art.

Therapeutic compounds are effective upon direct contact of the compound with the affected tissue. Accordingly, the compound is administered topically. Alternatively, the therapeutic compounds are administered systemically. For example, the compounds are administered by inhalation. The compounds are delivered in the form of an aerosol spray from pressured container or dispenser which contains a suitable propellant, e.g., a gas such as carbon dioxide, or a nebulizer.

Additionally, compounds are administered by implanting (either directly into an organ or subcutaneously) a solid or resorbable matrix which slowly releases the compound into adjacent and surrounding tissues of the subject.

Screening Assays

The invention also provides a method of screening for therapeutic targets for treating cancers. In particular, the invention provides a method for identifying therapeutic targets for treating cancer by providing a cell that is null for Wnt/β-catenin actrivating mutation.and contacting the cell with a library of RNAi. Potential therapeutic targets are identified by determining what RNAi is lethal to the cell.

Definitions

The term "polypeptide" refers, in one embodiment, to a protein or, in another embodiment, to protein fragment or fragments or, in another embodiment, a string of amino acids. In one embodiment, reference to "peptide" or "polypeptide" when in reference to any polypeptide of this invention, is meant to include native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into cells. Such modifications include, but are not limited to N terminal, C terminal or peptide bond modification, including, but not limited to, backbone modifications, and residue modification, each of which represents an additional embodiment of the invention. Methods for preparing peptidomimetic compounds are well known in the art and are specified, for example, in Quantitative Drug Design, C. A. Ramsden Gd., Chapter 17.2, F. Choplin Pergamon Press (1992).

As used interchangeably herein, the terms "oligonucleotides", "polynucleotides", and "nucleic acids" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, all as described herein.

The term "homology", when in reference to any nucleic acid sequence indicates a percentage of nucleotides in a candidate sequence that are identical with the nucleotides of a corresponding native nucleic acid sequence. Homology may be determined by computer algorithm for sequence alignment, by methods well described in the art. For example, computer algorithm analysis of nucleic acid or amino acid sequence homology may include the utilization of any number of software packages available, such as, for example, the BLAST, DOMAIN, BEAUTY (BLAST Enhanced Alignment Utility), GENPEPT and TREMBL packages.

As used herein, the term "substantial sequence identity" or "substantial homology" is used to indicate that a sequence exhibits substantial structural or functional equivalence with another sequence. Any structural or functional differences between sequences having substantial sequence identity or substantial homology will be de minimus; that is, they will not affect the ability of the sequence to function as indicated in the desired application. Differences may be due to inherent variations in codon usage among different species, for example. Structural differences are considered de minimus if there is a significant amount of sequence overlap or similarity between two or more different sequences or if the different sequences exhibit similar physical characteristics even if the sequences differ in length or structure. Such characteristics include, for example, the ability to hybridize under defined conditions, or in the case of proteins, immunological crossreactivity, similar enzymatic activity, etc. The skilled practitioner can readily determine each of these characteristics by art known methods.

Additionally, two nucleotide sequences are "substantially complementary" if the sequences have at least about 70 percent or greater, more preferably 80 percent or greater, even more preferably about 90 percent or greater, and most preferably about 95 percent or greater sequence similarity between them. Two amino acid sequences are substantially homologous if they have at least 50%, preferably at least 70%, more preferably at least 80%, even more preferably at least 90%, and most preferably at least 95% similarity between the active, or functionally relevant, portions of the polypeptides.

To determine the percent identity of two sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. As used herein, "ameliorated" or "treatment" refers to a symptom which is approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests.

Thus, treating may include suppressing, inhibiting, preventing, treating, or a combination thereof. Treating refers inter alia to increasing time to sustained progression, expediting remission, inducing remission, augmenting remission, speeding recovery, increasing efficacy of or decreasing resistance to alternative therapeutics, or a combination thereof. "Suppressing" or "inhibiting", refers inter alia to delaying the onset of symptoms, preventing relapse to a disease, decreasing the number or frequency of relapse episodes, increasing latency between symptomatic episodes, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof. The symptoms are primary, while in another embodiment, symptoms are secondary. "Primary" refers to a symptom that is a direct result of the proliferative disorder, while, secondary refers to a symptom that is derived from or consequent to a primary cause. Symptoms may be any manifestation of a disease or pathological condition.

The "treatment of cancer or tumor cells", refers to an amount of peptide or nucleic acid, described throughout the specification, capable of invoking one or more of the following effects: (1) inhibition of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

As used herein, "an ameliorated symptom" or "treated symptom" refers to a symptom which approaches a normalized value, e.g., is less than 50% different from a normalized value, preferably is less than about 25% different from a normalized value, more preferably, is less than 10% different from a normalized value, and still more preferably, is not significantly different from a normalized value as determined using routine statistical tests.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" or "therapeutic amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer to shrink rr or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, "cancer" refers to all types of cancer or neoplasm or malignant tumors found in mammals, including, but not limited to: leukemias, lymphomas, melanomas, carcinomas and sarcomas. Examples of cancers are cancer of the brain, breast, pancreas, cervix, colon, head and neck, kidney, lung, non-small cell lung, melanoma, mesothelioma, ovary, sarcoma, stomach, uterus and Medulloblastoma. Additional cancers include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

A "proliferative disorder" is a disease or condition caused by cells which grow more quickly than normal cells, i.e., tumor cells. Proliferative disorders include benign tumors and malignant tumors. When classified by structure of the tumor, proliferative disorders include solid tumors and hematopoietic tumors.

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

By the term "modulate," it is meant that any of the mentioned activities, are, e.g., increased, enhanced, increased, augmented, agonized (acts as an agonist), promoted, decreased, reduced, suppressed blocked, or antagonized (acts as an antagonist). Modulation can increase activity more than 1-fold, 2-fold, 3-fold, 5-fold, 10-fold, 100-fold, etc., over baseline values. Modulation can also decrease its activity below baseline values.

As used herein, the term "administering to a cell" (e.g., an expression vector, nucleic acid, a delivery vehicle, agent, and the like) refers to transducing, transfecting, microinjecting, electroporating, or shooting, the cell with the molecule. In some aspects, molecules are introduced into a target cell by contacting the target cell with a delivery cell (e.g., by cell fusion or by lysing the delivery cell when it is in proximity to the target cell).

As used herein, "molecule" is used generically to encompass any vector, antibody, protein, drug and the like which are used in therapy and can be detected in a patient by the methods of the invention. For example, multiple different types of nucleic acid delivery vectors encoding different types of genes which may act together to promote a therapeutic effect, or to increase the efficacy or selectivity of gene transfer and/or gene expression in a cell. The nucleic acid delivery vector may be provided as naked nucleic acids or in a delivery vehicle associated with one or more molecules for facilitating entry of a nucleic acid into a cell. Suitable delivery vehicles include, but are not limited to: liposomal formulations, polypeptides; polysaccharides; lipopolysaccharides, viral formulations (e.g., including viruses, viral particles, artificial viral envelopes and the like), cell delivery vehicles, and the like.

EXAMPLES

Example 1: Methods

Cell Proliferation Assays

Following shRNA infection and puromycin selection, 6000 cells were plated in 24 well plates in quadruplicates. 8 d later cells were fixed in 10% buffered formalin and stained with crystal violet (0.5% w/v). The crystal violet stain was quantified by addition of 10% (v/v) acetic acid.

Anchorage-Independent Growth Assays

Cancer cells (3 3 $10^5$) or HA1EM cells (7 3 $10^5$) were seeded in 0.3% Noble agar (Sigma, St. Louis) in 6-well plates, three replicates/sample. Bottom agar consisted of Dulbecco's Modified Eagle's Medium (DMEM) with 0.6% Noble agar, and 8% inactivated fetal calf serum. Colony formation was assessed at 3 wk and images of each well were taken at a 6.25× magnification using an Olympus SZX9 microscope equipped with an Olympus Qcolor 3 camera and the QCapture software. Images were analyzed using ImageJ software (NIH, Bethesda).

Small-Molecule Inhibitor Experiments 6000 cell/well were plated in 24-well plates and the indicated doses of dasatinib (Selleck, Houston) or vehicle was added 24 hr later. Proliferation was measured after 7 d by crystal violet staining.

Two-Class Permutation Analysis

The data from Project Achilles (Cheung et al., 2011) were analyzed using a two-class permutation analysis. Specifically we converted the results of massively parallel screening of 54,020 individual shRNAs targeting 11,194 genes to quantitative, gene-level scores using the ATARiS method (A.T., D.D.S., W.C.H., and J.P.M., unpublished data), which identifies sets of shRNAs that exhibit consistent proliferation effects across cell lines. We then used a two-class comparison analysis to detect genes that were significantly essential for the survival/proliferation of cell lines classified as β-catenin active. For each gene, we assigned a mean difference by calculating the mean dependency score for each gene within its designated class and finding the mean difference between classes. To assess the statistical significance of this calculated difference, we randomly permutated the cell lines between the two classes and assigned a new mean difference for each gene. This process was repeated 50,000 times and a p-value was assigned to each gene representing the likelihood that the particular gene distinguishes the two classes (the optimal p-value that can be achieved is $2 \times 10^{-5}$). To correct for multiple hypothesis testing, we generated False Discovery Rate q-values using the Benjamini-Hochberg method (Benjamini and Hochberg, 1995).

Plasmids

7TFC and 7TFP (Addgene 24308, 24307) were used for characterization of the 3-catenin/TCF4 reporter activity (Fuerer and Nusse, 2010). The following plasmids were obtained from Addgene: the FLAG-epitope tagged YAP1 (Addgene 17791) was described (Ko-muro et al., 2003) and Y357F YAP (Addgene 18882) was from (Levy et al., 2008) the HA-YAP1 (Addgene 27007) was from (Alarcón et al., 2009). For rescue experiments, WT or mutated YAP1 were cloned into pLX303. For soft agar experiments 5S YAP1 (Addgene 27371) (Zhao et al., 2007) or stabilized 3-catenin (Addgene 24313) (Fuerer and Nusse, 2010) were cloned into pLX303 (Yang et al., 2011). WT or dasatinib resistant YES1 were cloned into pLX303. WT SRC, SRC K295R and SRC Y527F were from Dr. Joan Brugge (Addgene 13665, 13659 and 13660). FYN expression vector (Addgene 16032) was from (Mariotti et al., 2001). For TBX5 interaction assays, we cloned a FLAG-epitope tagged version of TBX5 (Addgene 32968) (He et al., 2011) into pLX303.

shRNA and ORF Expression

The pLKO.1 vector was used to express shRNAs, and pLX303 was used to express ORFs. Lentiviruses were produced in 293T cells using the three-vector system as described (Moffat et al., 2006; Yang et al., 2011). The virus was diluted (1:15) and added to $2.5 \times 10^5$ cells in a 6 well plate containing 8 μg/ml of polybrene (Sigma). Plates were centrifuged for 15 min, 1178×g at RT. For selection of virally infected cells, 2 μg/ml of Puromycin or 5 μg/ml of Blastocidin was used 24 hr postinfection.

Immunoblotting

Cells were lysed using RIPA buffer (Cell Signaling, Beverly, MA) with the addition of protease and phosphatase inhibitors (Roche, Indianapolis, IN). Following lysis, cells were sonicated for 10 s and then centrifuged for 10 min at 4° C. The protein concentration of the lysate was quantified using the BCA protein quantitation kit (Pierce) and 30 μg of lysate was in SDS polyacrylamide gel electrophoresis (Invitrogen). The blots were probed with the indicated antibodies β-catenin (Cell signaling or BD PharMingen, Sparks, MD) YAP1 (Cell signaling, Beverly, MA), YES1 (BD Transduction, Chicago, IL), actin (Santa Cruz, Santa Cruz, CA), pY (Santa Cruz, Santa Cruz, CA), YAP1 pY357 (Abcam), SRC (Santa Cruz, Santa Cruz, CA), BCLXL (Cell Signaling Technology, Beverly, MA), BIRC5 (Cell Signaling Technology, Beverly, MA).

Reporter Assay

For the characterization of β-catenin activity in 85 cancer cell lines, cells were infected with a lentivirally delivered β-catenin reporter that harbors a puromycin selection marker, TFP (Fuerer and Nusse, 2010). Following Puromycin selection, 50,000 cells were plated in 96-well plates, and luciferase luminescence was measured using the Luc-Screen detection kit 24 hr later (Applied Biosystems, Carlsbad, CA). For characterization of the β-catenin activity following shRNA expression, the cells were infected with a lentivirally delivered β-catenin reporter harboring a mCherry selectable marker, TFC (Fuerer and Nusse, 2010) and after FACS sorting the same cells were infected with a Blastocidin-selectable LacZ expression vector. Following selection, the cells were infected with lentiviruses containing the indicated shRNAs. Luciferase and LacZ activity were measured 5 d postinfection using the Dual-light detection kit (Applied Biosystems, Carlsbad, CA). The Luciferase signal was normalized to that observed upon expression of LacZ.

Coimmunoprecipitation Assay

Lysis buffer [50 mM Tris-HCl pH=7.4, 150 mM NaCl, 1 mM EDTA, 0.5% Na-Deoxycholate (v/v), 1% Triton X-100 (v/v) containing protease inhibitors (Roche)] was added to cells. Following scraping, lysates were sonicated lightly and centrifuged for 10 min at 4° C. 2 mg of lysates was incubated overnight at 4° C. with a β-catenin (BD PharMingen) or YAP1 (Cell Signaling Technology) antibody. The lysates were then incubated for 2 hr at 4° C. with Dynabeads protein G (Invitrogen, Grand Island, NY) and then washed three times with wash buffer (50 mM Tris-HCl pH=7.4, 150 mM NaCl, 1% Triton X-100 (v/v)). The beads were then re-suspended with 2× sample buffer boiled for 5 min and analyzed by SDS-PAGE. Following SDS-PAGE separation and transfer to a nitrocellulose membrane, the blot was probed with either a β-catenin specific antibody (Cell Signaling Technology or BD PharMingen) or with a YAP1 specific anti-body (Cell Signaling Technology).

Immunofluorescence

The indicated cells were plated on a microscope slide at either a dense (100,000 cells/well) or sparse (10,000 cells/well) concentration. After 24 hr at 37° C., cells were fixed by adding 10% buffered formalin. Cells were permeabilized by adding 0.5% Triton in PBS (v v) for 15 min at room temperature. The slides were then washed with PBS and blocked for 2 hr with serum free protein block (Dako-Cytomation). Each well was incubated with a cocktail containing 1:50 anti-β-catenin (BD PharMingen) and 1:50 of anti-YAP1 (Cell signaling) for 2 hr at RT. Following three washes secondary mouse and rabbit fluorescent antibodies were added (1:400) and incubated for an additional h at RT. The slides were then washed and visualized using an Olympus BX50 microscope equipped with a Qi-maging Retiga EXi camera.

Chromatin Immunoprecipitation

Cells growing on monolayer were fixed for 15 min at RT with 1% formaldehyde. The crosslinking reaction was stopped by adding 2.5 M glycine and 10 min incubation at room temperature. Cells were washed twice with cold PBS and then were incubated with RIPA buffer (Cell Signaling Technology) containing protease inhibitors (Roche) for 20 min on ice. Cells were then scraped and soni-cated, and the lysates obtained were centrifuged at 9,300×g, 4° C. for 10 min, and 1 mg of the supernatant was incubated with 10 pl of either YAP1 (Santa Cruz) or β-catenin (BD PharMingen) antibody overnight at 4° C. The next day 50 μl of Dynabead protein G (Invi-trogen) were added for 2 hr at 4° C. The beads were then washed twice with cold RIPA following by 4 washes with wash buffer (100 mM Tris-HCl pH=8.5, 500 mM LiCl, 1% NP-40 (v/v), 1% deoxycholic acid (v/v). Beads were then washed again twice with RIPA buffer and beads were incubated with 50 μl of TE buffer. The DNA was then reverse cross-linked by adding 200 μl of Talianidis buffer [70 mM Tris-HCl pH=8, 1 mM EDTA, 1.5% SDS (w/v)] and incubating for 10 min at 65° C. The beads were then centrifuged and the supernatant containing DNA was collected. DNA was amplified with primers specific for BIRC5 or BCL2L1 and using the KOD polymerase kit (EMD). The primers for BIRC5 and BCL2L1 were chosen after analyzing these promoters for β-catenin binding sites identified by β-catenin ChIP-sequencing. Specifically, we isolated β-catenin-associated chromatin from four β-catenin dependent colon cancer cell lines (DLD1, LoVo, HT29 and HCT116) using an anti-β-catenin antibody (Santa Cruz Biotechnology, sc-7199). Twenty ng of ChIP DNA or whole-cell extract from three biological replicates were used to generate an Illumina sequencing library. Briefly, DNA fragments were end-repaired using the End-It DNA End-Repair Kit (Epicenter) and then a single "A" base was added using Klenow (NEB). The fragments were ligated with Illumina Indexed adaptors (TruSeq DNA Sample Prep Kits) using DNA ligase (NEB). The ligated product was selected for 300-400 bp on 2% agarose gel to remove the non-ligated adaptors and was subjected to 18 PCR cycles with Illumina PCR primer cocktail (TruSeq DNA Sample Prep Kits). PCR product was purified on 2% agarose gel to retain fragment between 300-400 bp. Library concentrations were quantified by Qubit fluorometer (Invitrogen) and by quantitative PCR (Kapa Biosystem). Two barcoded libraries were pooled and sequenced to 50 bp in a single lane on Illumina HiSeq2000 using standard procedures for cluster amplification and sequencing by synthesis using the latest versions of Illumina software (instrument: HCS 1.5.15.1-RTA 1.13.48, Pipeline: Illumina CASAVA 1.8.2). The MACs analysis method (Zhang et al., 2008) was used to call β-catenin occupied peaks.

Quantitative RT-PCR

RNA was harvested from cells using QiaShredder and RNeasy (QIAGEN). Complementary DNA was prepared using Advantage RT-for-PCR according to manufacturer's instructions (Clontech). Quantitative PCR was carried out using SYBR green (Applied Bio-systems).

In Vivo Orthotopic Tumor Model $4 \times 10^6$ HCT116 cells were injected into the flanks of immunodeficient mice (NCr Nude, Taconic). Tumors were extracted, cut into 1 $mm^3$ cubes, and implanted into a pouch created in the cecum of a second mouse. For experiments with inducible shRNAs, the mice were fed a doxycycline diet 2 days after cecal implantation. Tumors were examined 3 weeks postimplantation.

Three-Dimensional Primary Intestinal Organoid Culture

Colons from Apc flox/flox; villin-CreER mice were dissected lengthwise and washed in cold PBS. 0.5-1 cm segment per dish was minced extensively on ice and embedded in a 3D collagen gel by using a double-dish culture system (Ootani et al., 2009). Tamoxifen (Sigma, 2 μM in ethanol) or vehicle (ethanol) was applied on the day of initial plating for 7 days to generate APC null or WT organoids. Organoids were recovered from collagen gel by collagenase IV incubation followed by 0.05% trypsin/EDTA incubation to dissociate organoids into single cells. 5,000 cells per well were seeded into 96 well transwell plates (Fisher Scientific). Organoids were treated with the indicated concentration of dasatinib (in DMSO) for 7 days and were quantified by using CellTiter 96 AQueous One Solution Cell Proliferation Assay (Promega).

Zebrafish Experiments

Zebrafish were maintained according to institutional animal care and use committee (IACUC-BIDMC) protocols. Validated morpholinos (MO) (Gene-Tools, PhiloMath, OR) designed against the ATG site of YES1 (5'-CC TCTT-TACTCTTGACACAGCCCAT-3', SEQ ID NO: 1) (Jopling and Hertog, 2007) or YAP1 (5'-AGCAACATTAACAACT-CACTTTAGG-3', SEQ ID NO: 2) (Skouloudaki et al., 2009) were injected into WT or gut reporter (Tg(fabp2:RFP)as200) zebrafish at the one-cell stage. At 4 dpf, the gut morphology of intestinal reporter embryos was imaged by fluorescent microscopy (Discovery, Carl Zeiss). Whole-mount in situ hybridization experiments were conducted by using standard zebrafish protocols (http://zfin.org), and the gut tissue was visualized by using the established marker IFABP (Mudumana et al., 2004). The axin1$^{tm213}$ mutant line Masterblind was reared at 30° C. (temperature required for homozygote phenotype to be fully penetrant). Larvae were fixed overnight in 4% PFA, processed and embedded in JB-4 resin, cut into 7 mM sections, and stained with Hematoxylin and Eosin (Sullivan-Brown et al., 2011). The total number of intestinal epithelial cells and intestinal wall thickness was quantified in sections at a location of the intestinal bulb that had a comparable amount of pancreatic and liver tissue (20 sections quantified represent four sections of five animals).

Example 2: Identification of Essential Genes in WNT-B-Catenin Active Cell Lines

Figure 1:
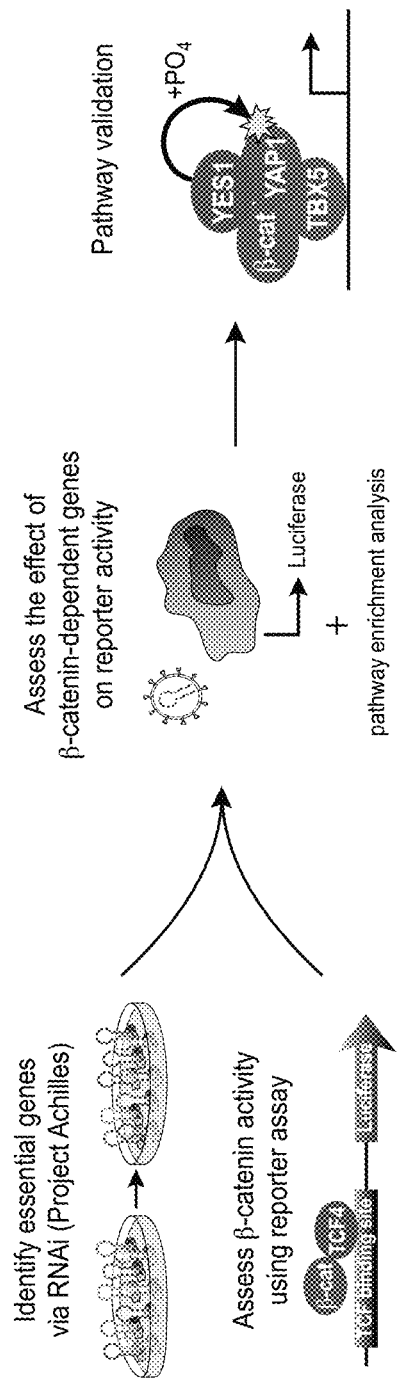
FIG. 1: Strategy to identify genes required in β-catenin-active cell lines. Schematic diagram depicting the strategy disclosed herein to identify genes required in β-catenin-active cell lines.

To identify genes whose expression is essential for the survival of cell lines that exhibit activated β-catenin, we used a lentivirally delivered β-catenin/TCF4 reporter to classify the activity of the Wnt/β-catenin pathway in 85 cancer cell lines in which we have performed genome scale loss of function screens, whole genome transcriptional profiling and global copy number analyses (FIG. 1). We first evaluated the specificity of this reporter in three colon cancer cell lines (DLD1, Colo205 and HCT116) that harbor mutations in components of the Wnt/β-catenin pathway and are dependent on this pathway for their survival. Specifically, we showed that the expression of two distinct CTNNB1-specific shRNAs suppressed β-catenin expression (FIG. 2A) and inhibited the β-catenin/TCF4 reporter activity in these cell lines (FIG. 2B), confirming that the activity of this reporter is dependent on β-catenin. We used this reporter to measure β-catenin activity in 85 cancer cell lines (FIG. 2C) and identified 19 cell lines, including 13 colon cancer cell lines that showed reporter activity that was 10-fold above background (Table 1). We note that two colon cancer cell lines known to harbor APC mutations (HT29 and LS411N) exhibited little β-catenin activity in this assay and were considered as reporter inactive.

Figure 2:
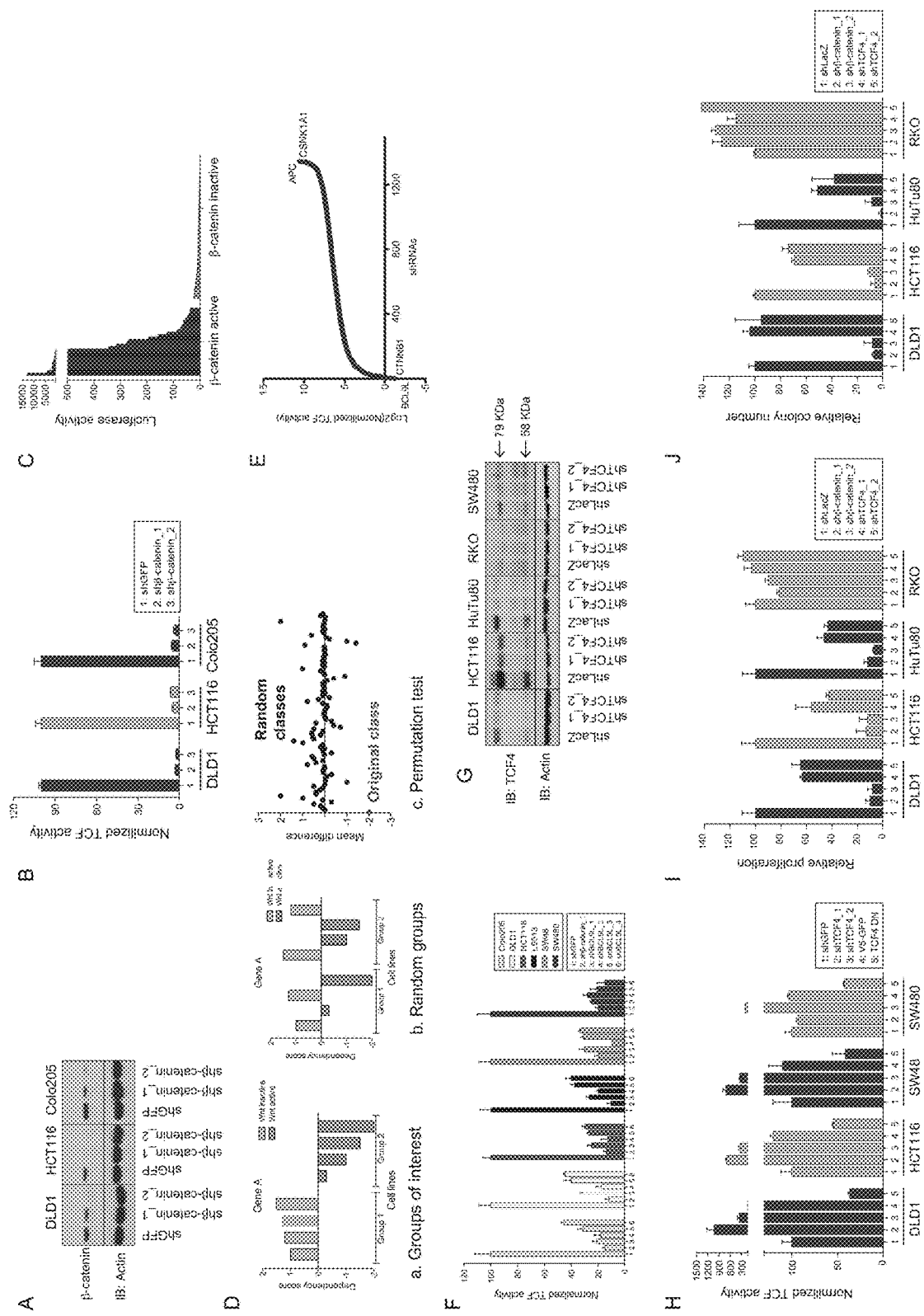
FIG. 2: Characterization of Wnt/β-catenin activity and identification of genes essential for Wnt/β-catenin active cell lines. (A) The indicated cell lines were infected with β-catenin targeting shRNAs and following selection the protein levels were measured by western blot analysis. (B) The β-catenin/TCF4 luciferase reporter and a constitutively active LacZ reporter were introduced into the indicated cell lines and following infection with the indicated shRNAs the levels of β-catenin/TCF4 reporter were measured. The LacZ signal was used for normalization. (C) β-catenin/TCF4 reporter activity in 85 cancer cell lines. (D) Scheme describing the two-class analysis used in this study. (E) DLD1 cells contacting the same reporters as in (B) were infected, in an arrayed format, with 750 shRNAs corresponding to 250 genes in quadruplicates. Five days post infection the β-catenin/TCF4 activity was measured and normalized to that of the LacZ signal. (F) Exactly as in (E) using the indicated cell lines and shRNAs. (G) The indicated cells were infected with TCF4 targeting shRNAs and following selection the protein levels were measured by immunoblot analysis. (H) As in (E) using the indicated cell lines and shRNAs. (I) The indicated cell lines were infected with shRNAs targeting either β-catenin or TCF4 and proliferation was measured 10 days post infection (J) or anchorage independent growth was measured after 3 weeks.

We then analyzed the proliferation/survival data from Project Achilles for these 85 cell lines. Specifically we converted the results of massively parallel screening of 54,020 individual shRNAs targeting 11,194 genes to quantitative, gene-level scores using the ATARiS algorithm, which identifies sets of shRNAs with similar behavior across all samples. We then used a two-class comparison analysis to detect genes that were significantly more essential for the survival/proliferation of cell lines that we considered to be β-catenin active (FIG. 2C, D). For each gene we assigned a mean difference by calculating the mean score for each gene within its designated group and finding the mean difference between groups. To assess the statistical significance of the mean difference, we randomly permutated the cell lines between the two groups and assigned a new mean difference for each gene. This process was repeated 50,000 times and the number of times that a random assignment was better than that of the original rankings was calculated. Based on this analysis, we assigned a p-value to each gene that represents the likelihood that the particular gene distinguishes the two groups (the optimal p-value that can be achieved is $2 \times 10^{-5}$). To correct for multiple hypothesis testing, the p-value is converted to a q-value based on the Benjamini Hochberg method. When we performed this analysis using cells randomly selected into two categories, we failed to identify any genes that distinguished the classes in a statistically significant manner (q<0.25). In contrast, when we classified the cell lines based on the mutational status of known oncogenes such as KRAS, BRAF or PIK3CA, we found that the specific oncogene scored as highest ranking gene that distinguished the two classes (Table 2). These observations demonstrate the utility of this method to find genes whose expression is required for the proliferation/survival of cell lines classified by specific features.

We applied this analytical method to cell lines classified by the reporter assay as β-catenin active or inactive and identified genes whose expression was essential for the survival/proliferation of β-catenin active cancer cell lines. As expected, we identified β-catenin as the top-scoring gene. In addition, we found 49 other genes that were significantly more essential for the proliferation/survival of β-catenin active cancer cell lines (q-value<0.25).

To determine whether any of these essential genes affected the activity of the β-catenin reporter, we used a less stringent criteria (q-value<0.47) and tested whether suppressing each of the top 250 genes that scored in the above analysis affected the activity of the Wnt/β-catenin reporter in the DLD-1 colon cancer cell line. Specifically, we introduced 3 independent shRNAs targeting each of these 250 genes in an arrayed format and identified 46 genes for which at least two shRNAs targeting the same gene inhibited the reporter activity by more than 50%. We then validated these findings by introducing these shRNAs into a larger panel of cell lines (FIG. 2E). As expected, suppression of destruction complex components, such as APC or CSNK1A1, induced increased reporter activity (FIG. 2E). Of these 250 genes, we found only 2 genes to be essential for the activity of the β-catenin reporter: β-catenin and BCL9L (FIG. 2F). Prior work identified BCL9L as a β-catenin binding protein that regulates its transcriptional activity. These observations indicated that the majority of the genes that we found to be essential in β-catenin active cell lines do not regulate the Wnt/β-catenin reporter but are instead genes essential in the context of active β-catenin.

β-catenin has been reported to bind to TCF/LEF family transcription factors to regulate gene expression. Since we failed to identify TCF4 as required for the survival of cell lines that exhibited β-catenin activity, we manipulated the expression of TCF4 using TCF7L2-specific shRNAs (FIG. 2G) or introduced a well-characterized dominantly interfering allele of TCF4. In consonance with prior studies, expression of the dominantly interfering TCF4 allele inhibited the reporter activity (FIG. 2H). In contrast, knockdown of TCF4 increased the activity of the β-catenin/TCF4 reporter activity (FIG. 2H), as has been recently been reported.

We then assessed the consequences of suppressing β-catenin or TCF4, on the proliferation and anchorage independent growth of colon cancer cell lines that expressed (HuTu80, DLD1 and HCT116) or failed to express (RKO) β-catenin/TCF4 reporter activity. As expected, suppression of β-catenin or TCF4 failed to affect the proliferation (FIG. 2I) or anchorage independent growth (FIG. 2J) of the RKO cell line and inhibited both the proliferation and anchorage independent growth in cell lines that exhibited robust reporter activity. In contrast to what we observed when we suppressed β-catenin, depletion of TCF4 inhibited the proliferation and anchorage independent growth of the 3 colon cancer cell lines by only 30-40% (FIGS. 2I and J). These observations indicate that TCF4 only partially contributes to β-catenin-driven proliferation and anchorage independent growth and suggests that β-catenin may act in a TCF4 independent manner to induce full transformation.

Based on these observations, we examined the list of the top 50 scoring genes (q<0.25), which were essential for the growth of β-catenin active cell lines to identify other genes that contribute to β-catenin transforming activity. We identified a striking enrichment for proteins that are related to the transcription factor YAP1 (Table 3). To eliminate the possibility that these genes scored merely because our list included a large number of colon cancer cell lines (Table 1), we tested whether these genes were also enriched when we classified cell lines based on other commonly mutated oncogenes in colon cancer. Specifically, when we classified these cell lines based on KRAS, BRAF or PIK3CA mutational status, we failed to find any enrichment for genes related to YAP1 (Table 2). These observations indicate that these essential genes were specific for β-catenin active cancer cell lines.

Figure 3:
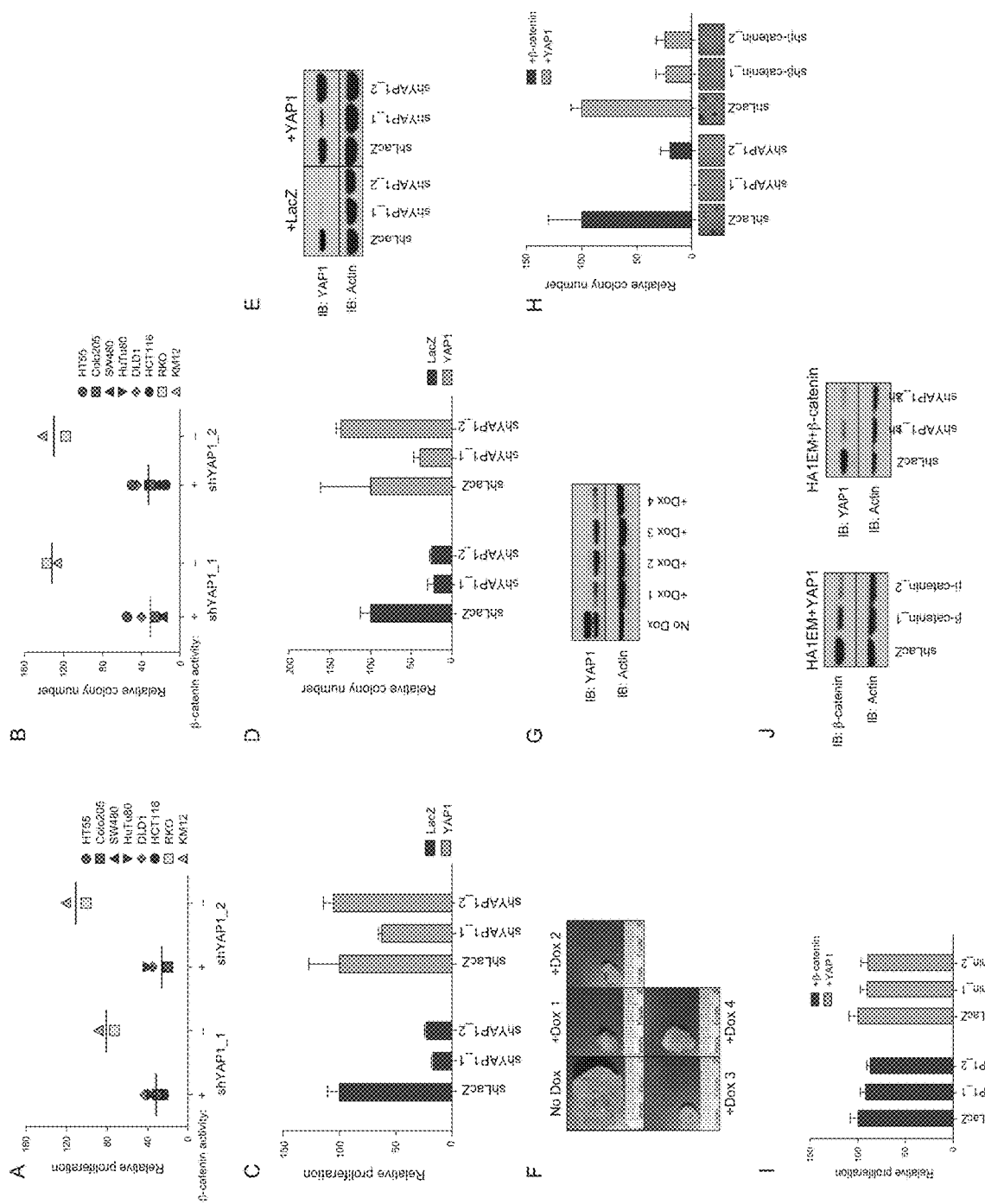
FIG. 3: YAP1 is essential for the growth of β-catenin dependent cancers. The indicated colon cancer cell lines were infected with shRNAs targeting YAP1 and proliferation (A) or anchorage independent growth (B) was assessed. The results were normalized to cells infected with a control shRNA targeting LacZ. (C) Proliferation and (D) anchorage independent growth and (E) protein levels of YAP1 were measures in HuTu80 cell lines overexpressing WT YAP1 and then infected with two shRNAs targeting YAP1. (F) Subcutaneous HCT116 tumors expressing a doxycycline inducible YAP1 shRNA were implanted into the cecum of nude mice and after 48 h were treated or not with doxycycline. Tumors were extracted three weeks post doxycycline treatment. (G) YAP1 protein levels of tumors in (F). HA1EM cells over expressing β-catenin or YAP1 were infected with shRNAs targeting YAP1 or β-catenin and anchorage independent growth (H) or proliferation (I) or protein levels (J) were measured.

Example 3: YAP1 is Essential for the Transforming Properties of WNT/β-Catenin Dependent Cancers The 65 kd Yes-associated protein, YAP1, is a transcriptional co-activator that can be regulated by several mechanisms including signaling from the Hippo pathway and tyrosine kinases such as YES1. YAP1 scored as essential for the proliferation/survival of β-catenin active cancer cell lines (Rank 32 q-value=0.24, Table 3). To confirm whether YAP1 was required for the proliferation and anchorage independent growth of colon cancer cell lines, we introduced 2 independent YAP1-specific shRNAs into a series of colon cancer cell lines and found that YAP1 expression was required for the proliferation and anchorage independent growth of cell lines that exhibited β-catenin activity (FIG. 3A, B and FIG. 12A). We also found that the HT29 and LS411N cell lines, which did not exhibit β-catenin/TCF4 activity (FIG. 2C) but harbor inactivating mutations of APC, were sensitive to suppression of either YAP1 or β-catenin (FIGS. 12B and C). To eliminate the possibility that the observed effects of the YAP1-specific shRNAs were due to off-targets effects of shRNAs, we expressed LacZ or YAP1 in parallel cultures of the HuTu80 cell line expressing control shRNAs or the two YAP1-specific shRNAs, one of which (shYAP1 2) targets the YAP1 3' untranslated region (UTR). We found that forced expression of YAP1 rescued the proliferation and anchorage independent growth of HuTu80 cells in which YAP1 was suppressed (FIGS. 3C, D and E).

The Yap-related protein TAZ has been reported to bind to YAP1 and also to regulate Wnt signaling by inhibiting dishevelled. To determine whether TAZ was required in cell lines that are depended on YAP1, we suppressed the expression of TAZ in β-catenin active cell lines (FIGS. 12D and E) and found no effect on cell proliferation. These observations indicate that TAZ is not required for YAP1 activity in this setting, perhaps because mutations that activate Wnt signaling in colon cancer are downstream of dishevelled.

In our initial validation studies, we demonstrated that suppression of YAP1 failed to affect the β-catenin reporter (FIG. 2E). Since YAP1 has been reported to affect β-catenin reporter activity in a colon cancer cell line, we suppressed YAP1 in 4 different colon cancer cell lines that harbor mutations in the Wnt/β-catenin pathway and failed to detect inhibition of reporter activity (FIG. 12F) or alterations in the transcription of known β-catenin/TCF4 target genes such as c-Myc, AXIN2 and SOX4 (FIG. 12G). In consonance with these observations, suppression of YAP1 failed to affect the stability of β-catenin (FIG. 12H).

To determine whether YAP1 was required for tumor maintenance in vivo, we developed an orthotopic colon cancer model in which tumors are obtained from subcutaneous xenografts derived from an established colon cancer cell lines and then implanted into the cecum of a second host. Orthotopic implantation of these tumors in the cecum resulted in tumors that infiltrated the murine colon and which metastasized to the liver of the host mice (FIG. 13A).

We used this model to determine whether β-catenin or YAP1 were required for tumor growth or maintenance. Specifically, we developed vectors that harbored doxycycline inducible shRNAs targeting either β-catenin or YAP1 and introduced these vectors into HCT116 cell lines in the absence of doxycycline. We implanted these cell lines subcutaneously and then transplanted the tumors into the cecum of recipient mice. After 2 days, we exposed mice to doxycycline to induce the expression of the indicated shRNAs and extracted the tumors 3 weeks later. We found that tumors expressing the inducible β-catenin-specific shRNAs showed diminished expression of β-catenin and were significantly smaller (FIGS. 13B and C). When we analyzed tumors expressing an inducible YAP1-specific shRNA, we found that suppression of YAP1 also inhibited tumor growth by 80-90% (FIGS. 3F and G), indicating that YAP1 is essential for tumor maintenance in vivo.

These observations confirm that YAP1 expression is required for the proliferation and tumorigenicity of Wnt/β-catenin active cell lines. To determine whether YAP1 contributes to cell transformation, we expressed a stabilized form of either β-catenin or YAP1 in HA1EM cells, a non-tumorigenic immortalized kidney epithelial cell line that can become tumorigenic by the forced expression of IKKε or AKT. Expression of β-catenin or YAP1 sufficed to promote anchorage independent growth of this cell line (FIG. 3H). These observations confirm that YAP1 expression transforms human cells to a similar degree as the expression of β-catenin.

We then tested whether β-catenin and YAP1 were required for the anchorage independent growth of cells expressing either β-catenin or YAP1. Suppression of YAP1 or β-catenin failed to affect the proliferation of cells transformed by the expression of either β-catenin or YAP1 (FIGS. 3I and J). However, suppression of β-catenin inhibited the anchorage independent growth of cells expressing YAP1, and suppression of YAP1 inhibited anchorage independent growth of cells expressing β-catenin (FIGS. 3H and J). Together these observations implicate YAP1 as an essential gene in β-catenin-mediated cell transformation and suggest that YAP1 and β-catenin cooperate to induce cell transformation.

Example 4: YES1 is Essential for the Transforming Properties of WNT/β-Catenin Dependent Cancers and Phosphorylates YAP1 on Tyrosine 357

YAP1 was originally identified as a Yes-associated protein. We also found the SRC family tyrosine kinase YES1 as a gene that was essential for the growth of Wnt/β-catenin active cell lines (rank 30, q-value=0.24, Table 3). As we found for YAP1, suppression of YES1 inhibited the proliferation, anchorage independent growth and tumor maintenance of β-catenin active colon cancer cell lines (FIG. 4A-D and FIG. 14A). Due to the sequence similarity between YES1 and SRC, we confirmed that YES1-specific shRNAs did not alter SRC protein levels (FIGS. 14A and B). Furthermore, shRNAs targeting SRC were not able to decrease the proliferation or anchorage independent growth of Wnt/β-catenin active cancer cell lines (FIG. 14C-E).

Figure 4:
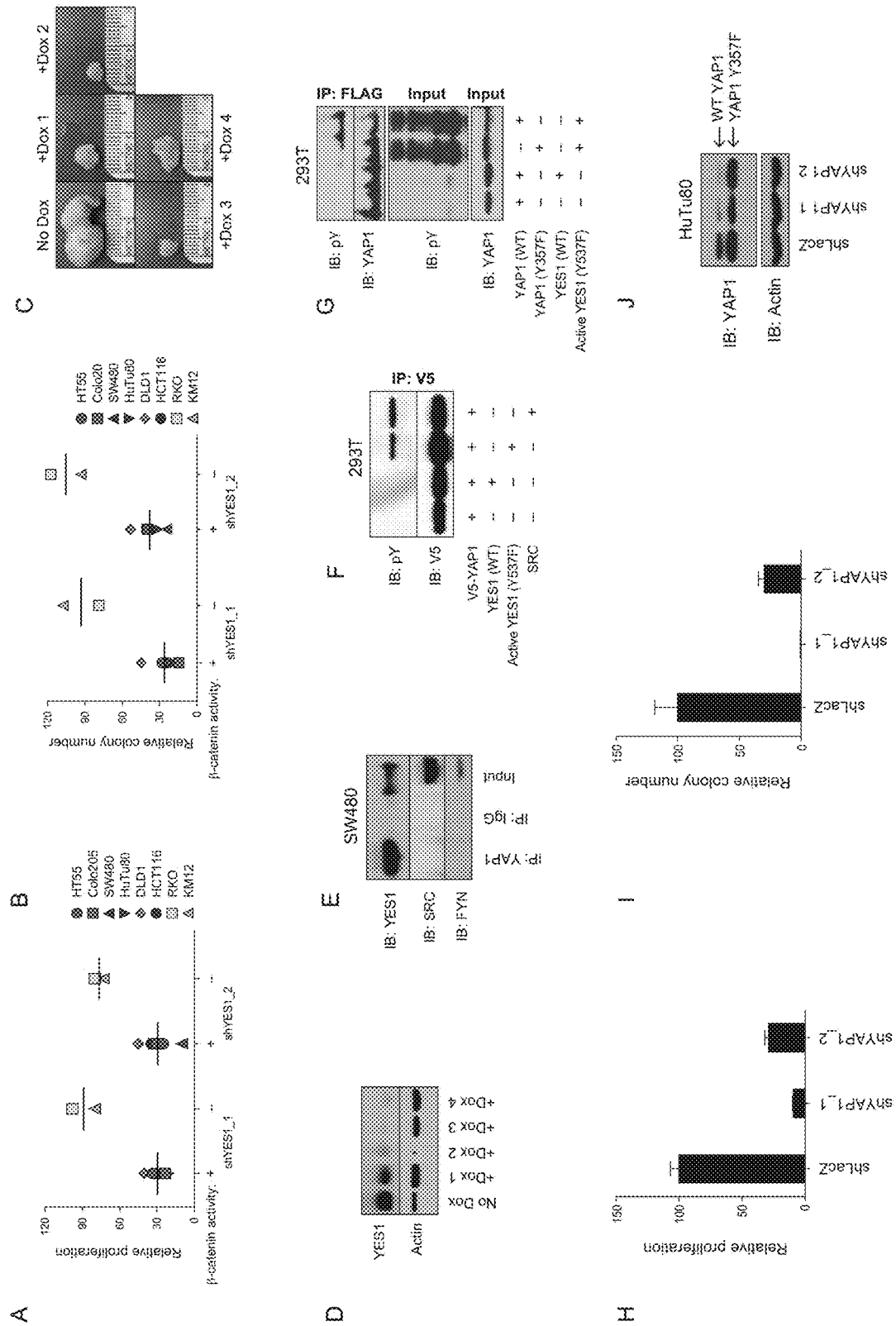
FIG. 4: YES1 is essential for the growth of Wnt/β-catenin active cancers and can phosphorylate YAP1 on tyrosine 357. The indicated colon cancer cell lines were infected with shRNAs targeting YES1 and proliferation (A) or anchorage independent growth (B) was assessed. The results were normalized to cells infected with a control shRNA targeting LacZ. (C) Subcutaneous HCT116 tumors expressing a doxycycline inducible YES1 shRNA were implanted into the cecum of nude mice and after 48 h were treated or not with doxycycline. Tumors were extracted three weeks post doxycycline treatment. (D) YES1 protein levels of tumors in (C). (E) YAP1 was immunoprecipitated from SW480 lystaes and following immunobloting the membrane was stained with the indicated antibodies. (F) 293T cells were transfected with a V5 tagged YAP1 and with the indicated SRC or YES1 plasmids. Following V5 IP the membrane was blotted with a phosphotyrosine antibody. (G) 293T cells were transfected with the indicated plasmids and following FLAG IP the membrane was blotted with the indicted antibodies. (H) Proliferation or anchorage independent growth (I) of Hutu80 cell lines expressing YAP1 Y357F and infected with shRNAs targeting YAP1. (J) YAP1 protein levels of cells in (H) and (I).

YAP1 binds YES1 and is phosphorylated by SRC family kinases in embryonic stem cells. We confirmed that YES1 and YAP1 interact in the β-catenin active colon cancer cell line, SW480 (FIG. 4E). Previous studies have shown that YAP1 is able to bind to other SRC family members such as SRC in HeLa cells. In colon cancer cell lines, we failed to detect an interaction between YAP1 and other SRC family members such as SRC and FYN (FIG. 4E). To determine whether YES1 and SRC phosphorylate YAP1, we expressed YAP1 in 293T cells and assessed YAP1 tyrosine phosphorylation when co-expressed with YES1 or SRC (FIG. 4F). We found that YAP1 was phosphorylated on tyrosine X by both WT or activated YES1 and SRC (FIG. 4F). In contrast, we did not observe any tyrosine phosphorylation of YAP1 when co-expressed with a kinase inactive SRC or with SRC in combination with a dominantly interfering SRC (FIG. 4F).

Figure 5:
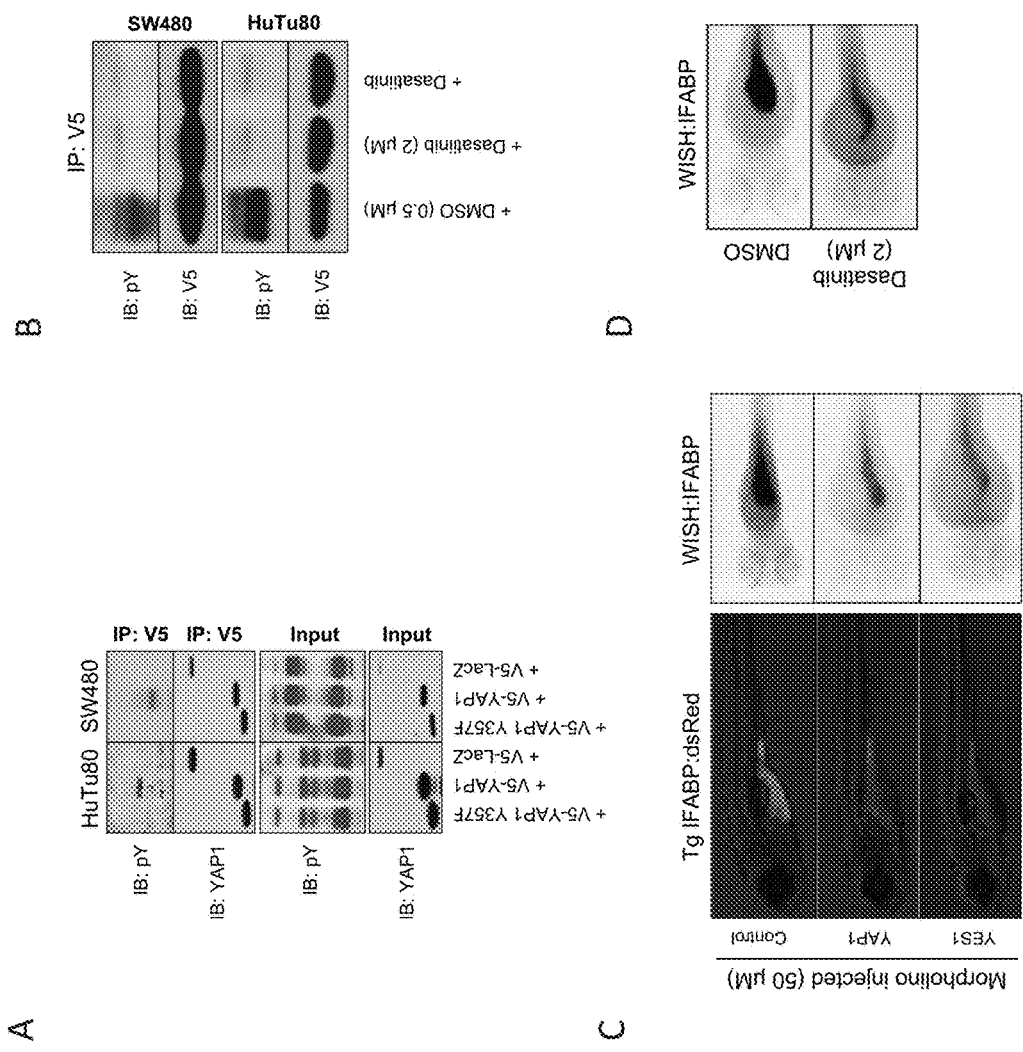
FIG. 5: YES1 is essential for tumorgenicity of β-catenin-active cells. (A) V5 immune complexes were isolated from HuTu80 or SW480 cells stably expressing WT or Y357F V5-epitope-tagged YAP1 or control V5-LacZ. Immune complexes were analyzed by immunoblotting with a phosphotyrosine antibody. (B) HuTu80 or SW480 cells stably expressing V5-epitope-tagged WT YAP1 were treated for 6 hr with 0.5 or 2 μM of dasatinib. V5 immune complexes were analyzed by immunoblotting with a phosphotyrosine antibody. (C) Transgenic IFABP:RFP zebrafish were injected with 50 μM of YAP1- or YES1-specific morpholinos. Red fluorescence was assessed 4 dpf, or IFABP expression was assessed 3 dpf by using whole-mount in situ hybridization with an IFABP-specific probe. (D) Embryos were exposed to 2 μM of dasatinib at 2 dpf, and IFABP expression was assessed after 24 hr by using whole-mount in situ hybridization.

Prior work has demonstrated that SRC family members phosphorylate tyrosine residues that are within a sequence motif that contains PXXY. YAP1 harbors only one tyrosine residue with this motif (tyrosine 357). Under conditions where YES1 or SRC phosphorylated YAP1, we failed to detect phosphorylation of the YAP1 Y357F mutant (FIGS. 4G and 5B). Importantly, although both YES1 and SRC were able to phosphorylate YAP1, suppression of SRC failed to inhibit the proliferation and anchorage independent growth of Wnt/β-catenin active cell lines (FIG. 14C-E). Thus we concluded that both YES1 and SRC phosphorylate YAP1 but only YES1 is essential for the survival of Wnt/β-catenin active colon cancers.

To determine whether YES1 or SRC phosphorylates YAP1, we expressed YAP1 in 293T cells and assessed YAP1 tyrosine phosphorylation when coexpressed with YES1 or SRC. We detected phosphorylated YAP1 only when YAP1 was coexpressed with SRC or with activated mutant version of YES1 (Y537F). We failed to detect phosphorylation of YAP1 when coexpressed with wild-type (WT) YES1, indicating that YAP1 phosphorylation requires the active form of YES1.

In 293T cells, we did not detect phosphorylated YAP1 when expressed alone. In contrast, we readily detected YAP1 tyrosine phosphorylation in HuTu80 or SW480 cells expressing WT YAP1 (FIG. 5A). Furthermore, treatment of colon cancer cells expressing WT YAP1 with the tyrosine kinase inhibitor dasatinib inhibited the tyrosine phosphorylation of YAP1 (FIG. 5B). These results confirm reported observations that demonstrated that YES1 is activated in colon cancer cell lines and tumors.

We then tested whether phosphorylation of tyrosine 357 was essential for YAP1 function. Specifically, when we expressed WT or Y357F YAP1 in HuTu80 cells expressing a YAP1-specific shRNA, we found that WT but not Y357F YAP1 was able to rescue the anti proliferative and anchorage independent growth effect of the YAP1-specific shRNA (compare FIG. 3C-D to FIG. 4H-I), despite equivalent levels of WT or mutant YAP1 expression (FIGS. 3E and 4J). Together these observations confirm that YES1 is essential for the tumorigenesis of β-catenin dependent cancers and suggests that its phosphorylation of YAP1 on tyrosine 357 regulates YAP1 activity.

To assess the relationship between YES1 and YAP1 in vivo, we examined the effect of suppressing these genes on zebrafish development. Microinjection of zebrafish embryos with a high concentration (200 μM) of YAP1- or YES1-specific morpholinos resulted in severe developmental phenotypes. Specifically, the YAP1 morphants developed craniofacial abnormalities and cardiac edema, whereas the YES1 morphants exhibited craniofacial abnormalities associated with pharyngeal defects (FIG. S5I). These phenotypes resemble defects observed when high concentrations of β-catenin-specific mor-pholinos were injected and confirm previous reports showing that YAP1 and YES1 are essential for early embryonic development in zebrafish.

Microinjection of YAP1 or YES1 morpholinos at lower doses (50 μM) avoided global toxicity but impaired gut development. Intestinal fatty-acid-binding protein (IFABP and FAPB2) is expressed in intestinal epithelial cells, where it plays a key role in gut metabolism and is used as a marker of gut development. Morpholino-mediated suppression of YAP1 or YES1 expression dramatically inhibited gut formation as determined by both fluorescence microscopy of Tg(fabp2:RFP)as200 gut reporter embryos and by examination of IFABP expression by in situ hybridization (FIG. 5C).

Furthermore, treatment of zebrafish embryos postfertilization (dpf) with 2 μM dasatinib inhibited gut formation to a similar extent as the YAP1- or YES1-specific morpholinos (FIG. 5D), indicating that YES1 kinase activity is essential for zebrafish gut development. Because the Wnt/β-catenin pathway has been shown to be crucial for gut development in zebrafish, we concluded that phosphorylation of YAP1 by YES1 is essential for developmental and malignant processes that are dependent on the function of β-catenin.

Previous studies have shown that, in response to cell contact inhibition, activation of the Hippo pathway induces serine 127 phosphorylation and cytosolic accumulation of YAP1. By using immunofluorescence, we found that both YAP1 and β-catenin were constitutively localized in the nucleus in colon cancer cell lines regardless of cell density or β-catenin activity (FIG. 6C) and that suppression of β-catenin failed to alter YAP1 localization (FIG. 15). Collectively, these observations suggest that, in contrast to nontransformed cell lines, culture density does not regulate YAP localization in colon cancer cell lines.

Example 5: YAP1 and β-Catenin Form a Complex That is Dependent on YES1 Phosphorylation of YAP1

Figure 6:
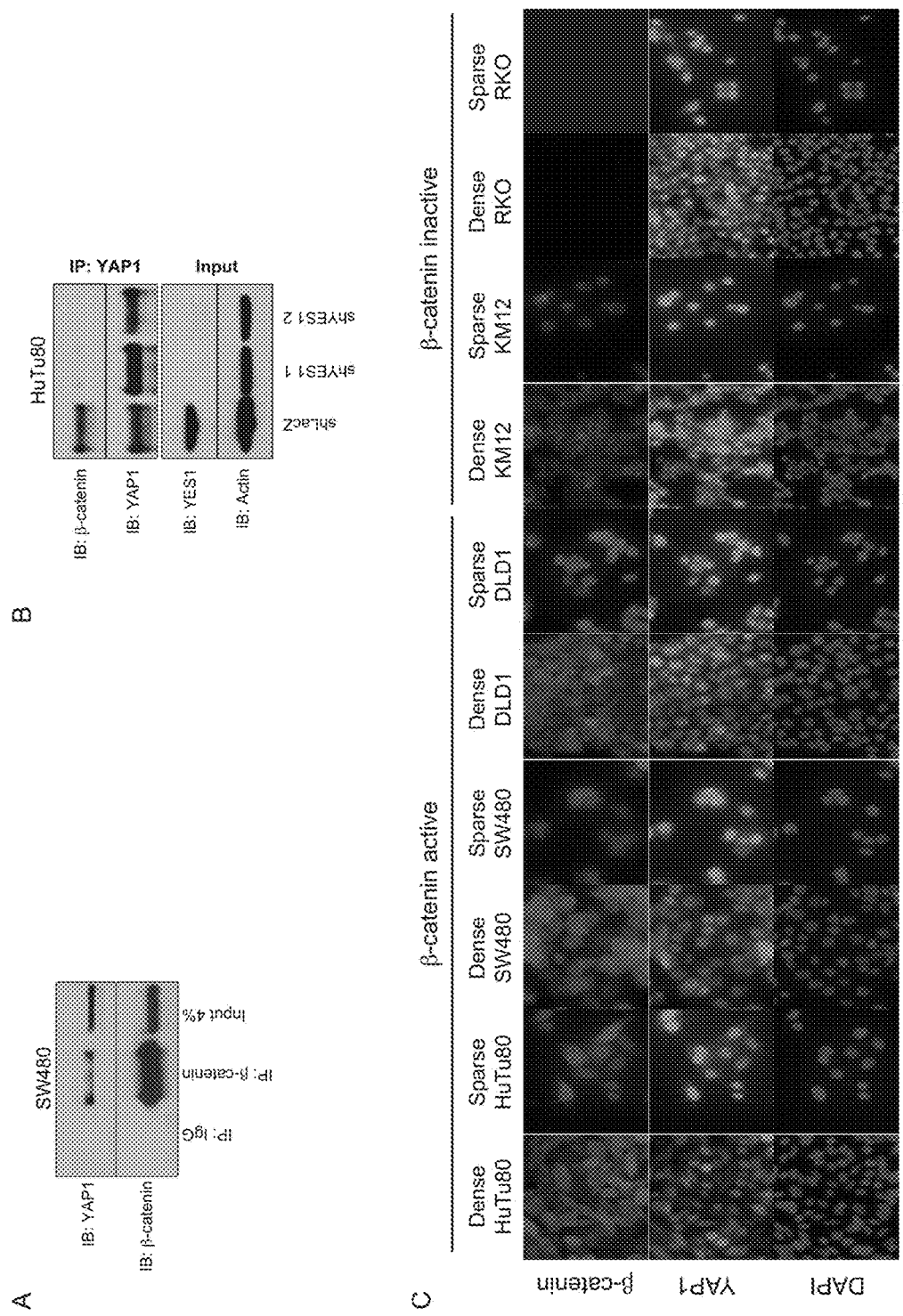
FIG. 6: YAP1 can form a complex with β-catenin that is dependent on YES1. (A) β-catenin or control IgG antibodies were incubated with lysates from SW480 cells and following running an SDS gel and transfer to a nitrocellulose membrane the blot was probed with an anti-YAP1 antibody. (B) Lysates from HuTu80 cells were treated with YES1 or control shRNAs and incubated with anti-YAP1 antibodies. Following SDS gel separation and transfer to a nitrocellulose membrane the blot was probed with a β-catenin antibody. (C) The indicated cancer cell lines were grown in dense or sparse cultures and the localization of β-catenin and YAP1 was evaluated by immunofluorescence.

A recent study demonstrated that YAP1 and β-catenin form a complex that plays a role in embryonic heart development. Using SW480 and HuTu80 colon cancer cell lines, we confirmed that endogenous YAP1 and β-catenin interact (FIGS. 6A and B). Specifically, we found that β-catenin-specific but not control immunoglobulin immune complexes contained YAP1 in SW480 lysates (FIG. 6A). Moreover, when we isolated YAP1-specific immune complexes, we could detect β-catenin (FIG. 6B).

To determine whether the interaction between β-catenin and YAP1 was regulated by YES1, we expressed two independent YES1-specific shRNAs in HuTu80 cells and found that suppression of YES1 abrogated the formation of the β-catenin-YAP complex (FIG. 6B). Furthermore, treatment of colon cancer cells with the tyrosine kinase inhibitor dasatinib which inhibits the kinase activity of YES1 and other tyrosine kinases inhibited the formation of the β-catenin-YAP1 complex (FIG. 6C). Based on these observations, we concluded that YAP1 and β-catenin form a complex in colon cancer cell lines that is dependent on phosphorylation of YAP1 by YES1.

Activation of the Hippo pathway has been reported to inhibit the nuclear localization of YAP1 in response to cell contact inhibition. To assess the subceullular localization of YAP1 and β-catenin in colon cancer cell lines, we performed immunofluorescence and found that both YAP1 and β-catenin were consistently located in the nucleus regardless of cell density (FIG. 6D and FIG. 15). Indeed, we found that YAP1 was localized to the nucleus whether or not these cells exhibited β-catenin activity (FIG. 6D). Moreover, suppression of β-catenin failed to alter YAP1 localization (FIG. 15). Collectively these observations suggest that in colon cancer cell lines YAP resides primarily in the nucleus.

Figure 7:
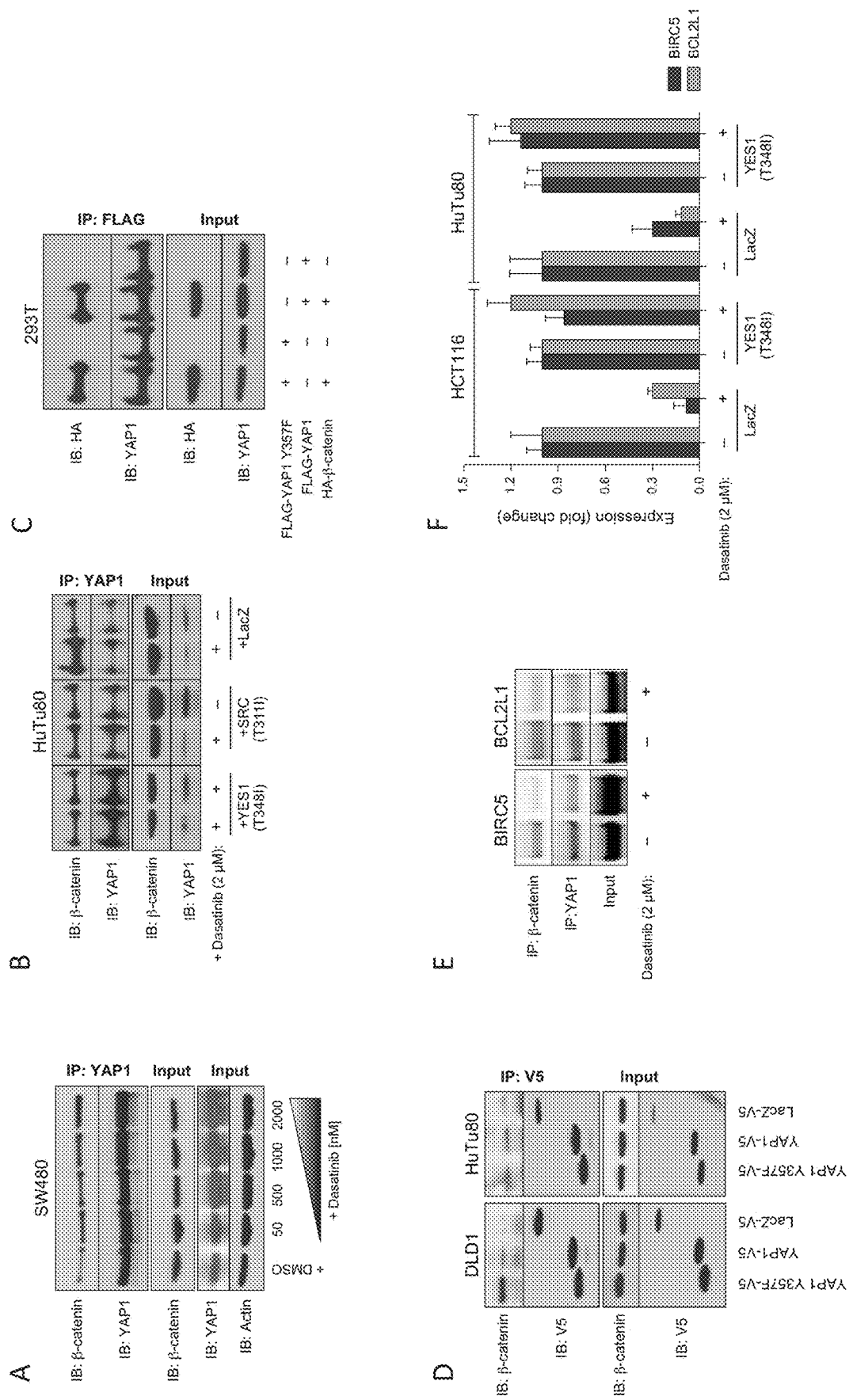
FIG. 7: Expression of YES1 is essential for formation of the YAP1-β-catenin-TBX5 complex. (A) SW480 cells were treated for 6 hr with increasing concentrations of dasatinib, and β-catenin-YAP1 complexes were assessed as in FIG. 6B. (B) HuTu80 cells expressing dasatinib-resistant YES1 or SRC mutants were treated with 2 μM of dasatinib for 6 hr, and the β-catenin-YAP1 interaction was assessed as in (A). (C) 293T cells were transfected with FLAG-epitope-tagged WT or Y357F YAP1 (5 μg) with or without HA-epitope-tagged β-catenin. FLAG immune complexes were assessed for the presence of HA-tagged proteins. (D) V5 immune complexes were isolated from DLD1 or HuTu80 colon cancer cell lines stably expressing V5-epitope-tagged WT or Y357F YAP1 or control LacZ, and the presence of β-catenin was assessed by immunoblotting. (E) β-catenin or YAP1 immune complexes from HCT116 cells treated with 2 μM of dasatinib or vehicle (DMSO) were subjected to ChIP analysis. (F) mRNA levels of BCL2L1 and BIRC5 in HCT116 or HuTu80 cells treated for 1 hr with 2 μM of dasatinib. Error bars represent mean±SD.

Example 6: YES1 Kinase Activity Regulates the Activity of the YAP1-β-Catenin-TBX5 Complex To determine whether the interaction between β-catenin and YAP1 was regulated by YES1, we expressed two distinct YES1-specific shRNAs in HuTu80 cells and found that suppression of YES1 expression abrogated the formation of the I3-catenin-YAP1 complex (FIG. 7A).

Treatment of zebrafish embryos with dasatinib, which inhibits YES1, resulted in a similar phenotype to that of suppressing YES1 expression (FIGS. 5E and F). Thus, we used dasatinib to test whether YES1 kinase activity was essential for the β-catenin-YAP1 interaction. In contrast to what we observed when we suppressed YES1 expression, treatment of the SW480 colon cancer cell line with dasatinib increased the interaction between β-catenin and YAP1, indicating that YES1 kinase activity is not required for formation of the β-catenin-YAP1 complex (FIG. 7B). The dasatinib-induced increase in β-catenin-YAP1 interaction was reversed by expression of a dasatinib-resistant form of YES1 or SRC (FIG. 7C). Furthermore, we found that the YAP1 mutant (YAP1 Y357F), which cannot be tyrosine phosphorylated, interacted with β-catenin when expressed in 293T cells or in colon cancer cell lines (FIGS. 7D and E). Thus, the interaction of YES1 with YAP1 and β-catenin is essential for formation of the β-catenin-YAP1 complex in a manner independent of YES1 kinase activity.

Because YES1 suppression disrupted the activity of the β-catenin-YAP1-TBX5 complex, we tested whether YES1 kinase activity was required for binding of the β-catenin-YAP1-TBX5 complex to specific target promoters. Treatment of HCT116 cells with dasatinib inhibited the binding of β-catenin and YAP1 to the BCL2L1 and BIRC5 promoters (FIG. 6F). Moreover, treatment of HCT116 or HuTu80 with dasatinib resulted in down-regulation of BCL2L1 and BIRC5 expression, which was reversed by expression of a dasatinib-resistant form of YES1 (FIG. 6G). These observations suggest that phosphorylation of YAP1 by YES1 is required for the activity of the β-catenin-YAP1-TBX5 complex.

Example 7: TBX5 Mediates the Binding of the B-Catenin-YAP1 Complex to DNA

Figure 9:
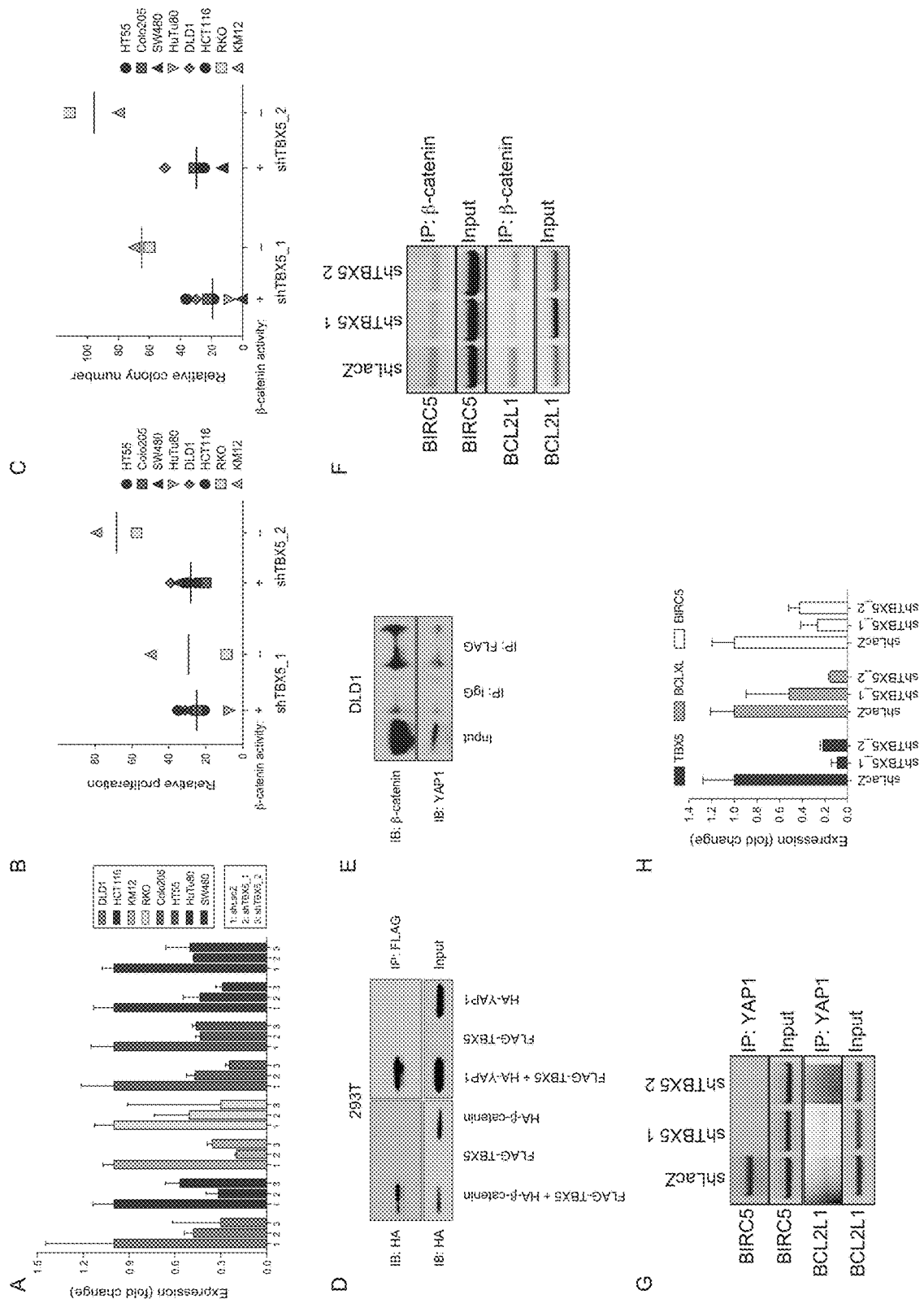
FIG. 9: TBX5 mediates the interaction of the YAP1-β-catenin complex to DNA.

Both YAP1 and β-catenin are transcriptional co-regulators. When we re-examined the list of genes that were specifically required in β-catenin reporter assay active cells, we noted that the TBX5 transcription factor that has been reported to be related to YAP ranked highly (Rank 8 q-value=0.1, Table 3). To confirm whether TBX5 was required for the proliferation and anchorage independent growth of β-catenin active colon cancer cell lines, we used TBX5-specific shRNAs that suppressed the mRNA levels of TBX5 by 30-50% (FIG. 9A). TBX5 suppression resulted in a specific decrease in proliferation and anchorage independent growth of β-catenin active colon cancer cell lines (FIGS. 9B and C). To determine whether TBX5 binds to YAP1 and β-catenin, we isolated TBX5-specific immune complexes from 293T or DLD1 cells and found that TBX5 binds to both β-catenin and YAP1 (FIGS. 9D and E). To determine whether TBX5 mediates the binding of the β-catenin-YAP1 complex to DNA, we performed chromatin immunoprecipitation experiments with X and Y. Specifically, expression of TBX5-specific shRNAs in HuTu80 cell lines inhibited the binding of β-catenin (FIG. 9F) or YAP1 (FIG. 9G) to the promoter regions of BCL2L1 and BIRC5. These observations suggest that the binding of the β-catenin-YAP1 complex to DNA is mediated by TBX5.

Example 8: BCL2L1 and BIRC5 are Transcriptional Targets of the YAP1-β-Catenin Complex and are Required for the Tumorigenicity of WNT/β-Catenin Dependent Cancers Among the genes that scored as significantly required for the survival of cell lines that exhibit β-catenin activity were BIRC5 (survivin) and BCL2L1 (Table 2). We confirmed that these genes were essential for the proliferation and anchorage independent growth of Wnt/β-catenin dependent cancer cell lines. Using shRNAs specific for BIRC5 or BCL2L1 (FIGS. 16A and B), we demonstrated that depletion of BIRC5 or BCL2L1 resulted in impaired proliferation and anchorage independent growth of Wnt/β-catenin dependent cancer cell lines (FIGS. 8A and B).

We hypothesized that BIRC5 and BCL2L1 are transcriptional targets of the β-catenin-YAP1 complex. To test this hypothesis, we examined the mRNA levels of BIRC5 and BCL2L1 in two colon cancer cell lines (HT55 and HCT116) in which we had suppressed either YAP1 or β-catenin and found that the expression of both BIRC5 and BCL2L1 are dependent on the presence of β-catenin and YAP1 (FIGS. 8C and D). Furthermore, when we suppressed YES1, we also found reduced levels of BIRC5 and BCL2L1 (FIGS. 8C and D) suggesting that the β-catenin-YAP1 complex is involved in transcriptional regulation of these genes.

To determine whether BCL2L1 and BIRC5 contribute to the proliferation arrest phenotype observed following suppression of either β-catenin or YAP1 in Wnt/β-catenin active cancer cell lines, we stably expressed the anti-apoptotic isoform of BCL2L1, BCL-XL or BIRC5 in a β-catenin active colon cancer cell line. Following overexpression of these genes, we expressed YAP1- or β-catenin-specific shRNAs. Ectopic expression of BCL-XL or BIRC5 rendered the levels of these proteins independent of β-catenin or YAP1 (FIG. 8E) and partially restored the proliferation of cell lines in which we suppressed either β-catenin or YAP1 (FIG. 8F), suggesting that these genes are targets of the β-catenin-YAP complex.

Figure 8:
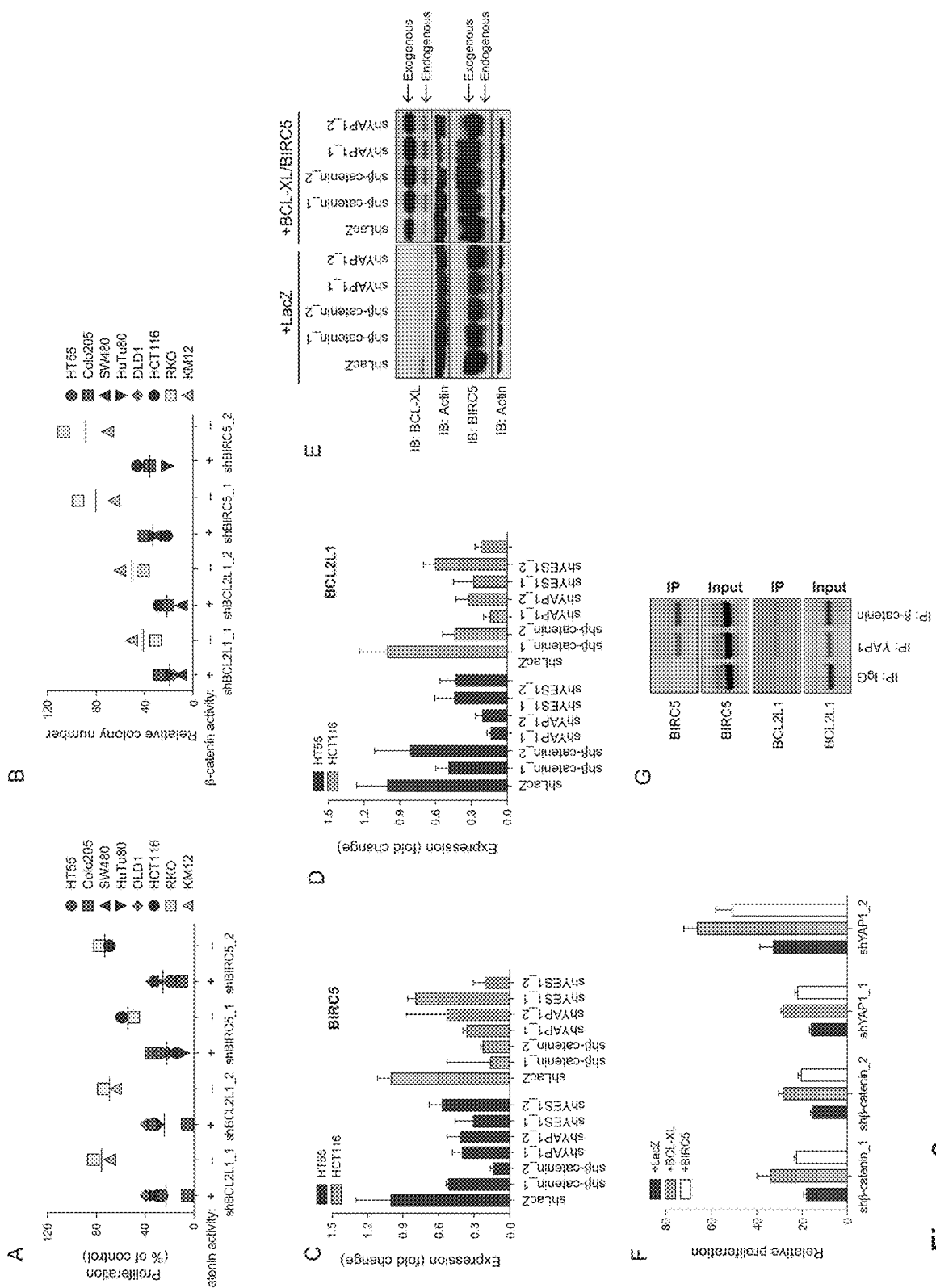
FIG. 8: BCL2L1 and BIRC5 are transcriptional targets of the YAP1-β-catenin complex and are essential for the survival of Wnt/β-catenin active cancers. The indicated colon cancer cell lines were infected with shRNAs targeting BCL2L1 or BIRC5 and proliferation (A) or anchorage independent growth (B) was assessed. The results were normalized to cells infected with a control LacZ targeting shRNA. (C and D) RNA was extracted from HT55 or HCT116 cell lines infected with shRNAs targeting β-catenin or YAP1 and subjected to quantitative RT-PCR analysis using BCL2L1 and BIRC5 specific primers. (E) HuTu80 cells overexpressing BCL-XL or BIRC5 or LacZ were infected with shRNAs targeting YAP1 or β-catenin and BCL-XL or BIRC5 protein levels were measured. (F) Proliferation of cell lines in (E). (G) Lysates from HuTu80 cells were incubated with anti-β-catenin, anti-YAP1 or anti-IgG and subjected to CHIP analysis with primers for the promoter region of BCL2L1 and BIRC5.

To confirm that β-catenin and YAP1 directly regulate BCL2L1 and BIRC5 expression, we performed a chromatin immunoprecipitation assay and found that both β-catenin and YAP1 were able to bind to the promoter regions of BCL2L1 and BIRC5 (FIG. 8G). Taken together these observations indicate that the YAP-β-catenin complex directly regulates the expression of these anti-apoptotic genes.

Example 9: WNT/β-Catenin Active Cancers are Sensitive to Small Molecule Inhibitors of the SRC Family The observation that the β-catenin-YAP1 complex promotes survival of cancer cells by inducing the transcription of the anti-apoptotic genes BCL2L1 and BIRC5 suggests that disrupting the activity of this complex would selectively affect β-catenin active cancers. To test this hypothesis, we tested whether colon cancer cell lines that exhibited β-catenin activity were more sensitive to the tyrosine kinase inhibitor dasatinib. Indeed, we found that β-catenin active cell lines were highly sensitive to exposure to dasatinib (FIG. 10A and Table 4).

Since dasatinib has broad activity for many tyrosine kinases, we tested whether the observed effects on cell proliferation were due to its effects on SRC family members. Importantly, similar to our observations with YAP1- and β-catenin-specific shRNAs, exposure of cells to dasatinib induced a proliferation arrest only after prolonged exposure (7 days). To determine this inhibition of SRC family members was dependent on the inhibition of SRC or YES, we expressed dasatinib resistant YES1 or SRC mutant in cells. We found that expression of either of these mutants rescued the proliferation arrest induced by dasatanib growth arrest (FIG. 10B-D). The observations confirm that inhibition of SRC and YES inhibit the proliferation of β-catenin active cell lines.

To corroborate these findings, we investigated the effects of inhibiting YES1 in colonic organoids and zebrafish. Primary colon organoids can be propagated in vitro as explants in air-liquid interface cultures Under these conditions, colon organoids recapitulate multilineage differentiation and Lgr5$^+$ intestinal stem cells. We cultured colon organoids from Apc$^{flox/flox}$; villin-CreER mice, which were exposed to tamoxifen in vitro to delete Apc. These WT or Apc null organoids were then treated with dasatinib (1-100 nM). We found that Apc null organoids were (p<0.005) more sensitive to dasatinib than WT organoids (FIGS. 11A and 11B). Specifically, we observed a 70% decrease in growth of APC null organoids treated with 50 nM of dasatinib compared to a 5% growth inhibition of WT organoids treated with dasatinib (FIG. 11B). These observations demonstrate that inhibition of YES1 kinase activity in APC null epithelium reverses the hyperproliferation induced by APC loss.

Stabilization of β-catenin in AXIN1 temperature-sensitive mutant zebrafish (Masterblind) induces a β-catenin-dependent hyperproliferation of intestinal epithelial cells (Cheesman et al., 2011). By using this model, we treated WT or AXIN1 mutant zebrafish at 6 dpf with 2 µM dasatinib for 48 hr, which suppressedintestinal hyperplasia in the AXIN1 mutants as assessed by morphology (FIG. 11C) or hematoxylin and eosin staining (H&E) (FIG. 11D). Furthermore, the number of epithelial cells was significantly (p<0.0001) decreased in AXIN1 mutant zebrafish treated with dasatinib (FIG. 11E). In contrast, we failed to observe changes in the intestinal structure or cell number in WT zebrafish treated with dasatinib, indicating that the effect of dasatinib was specific to AXIN1 mutant animals (FIGS. 11C and 11D). We concluded that inhibition of YES1 kinase activity inhibits the β-catenin-dependent proliferation in cultured human cancer cells, in colon epithelial organoids, and in a zebrafish model of intestinal hyperplasia.

TABLE 1

Cancer cell lines profiled for β-catenin activity.

| Origin | Wnt inactive | Wnt active |
|---|---|---|
| Colon | 6 | 13 |
| Esophageal | 8 | 1 |
| Liver | 1 | |
| Bone | 1 | |
| Gastric | 0 | 2 |
| Pancrease | 9 | |
| Ovarian | 20 | 1 |
| GBM | 6 | |
| Lung | 7 | 1 |
| Meningioma | 2 | 1 |
| Endometrium | 1 | |
| Multiple myeloma | 1 | |
| Melanoma | 1 | |
| Osteosarcoma | 1 | |
| Breast | 2 | |

TABLE 2

Significance scores for genes related to YAP1 following classification of cell lines by the mutational status of PIK3CA, BRAF and KRAS.

| PIK3CA mut vs. Rest | | | | BRAF mut vs. rest | | | | KRAS mut vs. rest | | | |
|---|---|---|---|---|---|---|---|---|---|---|---|
| Rank | Gene | p-value | q-value | Rank | Gene | p-value | q-value | Rank | Gene | p-value | q-value |
| 1 | PIK3CA | $2*10^{-5}$ | 0.04 | 1 | BRAF | $2*10^{-5}$ | 0.14 | 1 | KRAS | $2*10^{-5}$ | 0.02 |
| 269 | YAP1 | 0.01 | 0.38 | 283 | YAP1 | 0.047 | 0.97 | 249 | YAP1 | 0.02 | 0.77 |
| 2573 | YES1 | 0.32 | 0.91 | 868 | YES1 | 0.14 | 0.97 | 3098 | YES1 | 0.42 | 0.98 |
| 329 | BIRC5 | 0.01 | 0.4 | 508 | BIRC5 | 0.09 | 0.97 | 2336 | BIRC5 | 0.31 | 0.97 |
| 144 | BCL2L1 | 0.006 | 0.3 | 1442 | BCL2L1 | 0.23 | 0.97 | 218 | BCL2L1 | 0.02 | 0.74 |
| 2728 | TBX5 | 0.34 | 0.92 | 2290 | TBX5 | 0.35 | 0.97 | 1273 | TBX5 | 0.16 | 0.95 |
| 2723 | FAT1 | 0.34 | 0.92 | 2208 | FAT1 | 0.34 | 0.97 | 246 | FAT1 | 0.02 | 0.77 |

TABLE 3

Significance scores for genes related to YAP1 following classification of cell lines by β-catenin activity.

| Gene | q-value | Rank |
|---|---|---|
| YAP1 | 0.24 | 32 |
| YES1 | 0.24 | 30 |
| TBX5 | 0.1 | 8 |
| BIRC5 | 0.22 | 27 |
| FAT1 | 0.16 | 16 |
| BCL2L1 | 0.04 | 1 |

TABLE 4

IC50 of dasatinib in colon cancer cell lines.

| Cell line | Status of β-catenin pathway | IC50 Dasatinib (nM) |
|---|---|---|
| Colo205 | active | 80 |
| HCT116 | active | 68 |
| HT55 | active | 70 |
| HuTu80 | active | 70 |
| DLD1 | active | 125 |
| SW480 | active | 50 |
| KM12 | Non-active | >800 |
| RKO | Non-active | >800 |

What is claimed is:

1. A method of reducing YES1 activity thereby treating a Wnt/β-catenin active cancer in a human subject in need thereof, the method consisting of administering to the human subject a therapeutic amount of dasatinib effective to reduce YES1 activity, wherein the Wnt/β-catenin active cancer is colon cancer, breast cancer, lung cancer, leukemia, prostate cancer, skin cancer, liver cancer, ovarian cancer, brain cancer, or parathyroid cancer.

2. A method of reducing YES1 activity thereby treating a Wnt/β-catenin active cancer in a human subject in need thereof, the method consisting of administering to the human subject a therapeutic amount of dasatinib effective to reduce YES1 activity, wherein a level of β-catenin in the Wnt/β-catenin active cancer is unaffected upon administering the YES1 inhibitor.

3. The method of claim 2, wherein the Wnt/β-catenin active cancer is colon cancer, breast cancer, lung cancer, leukemia, prostate cancer, skin cancer, liver cancer, ovarian cancer, brain cancer, or parathyroid cancer.

4. The method of claim 1, wherein the mutational status of KRAS in the Wmt/β-catenin active cancer is normal.

5. The method of claim 1, wherein the Wnt/β-catenin active cancer is colon cancer.

6. The method of claim 1, wherein the Wnt/β-catenin active cancer is breast cancer.

7. The method of claim 1, wherein the Wnt/β-catenin active cancer is lung cancer.

8. The method of claim 1, wherein the Wnt/β-catenin active cancer is leukemia.

9. The method of claim 1, wherein the Wnt/β-catenin active cancer is prostate cancer.

10. The method of claim 1, wherein the Wnt/β-catenin active cancer is skin cancer.

11. The method of claim 1, wherein the Wnt/β-catenin active cancer is liver cancer.

12. The method of claim 1, wherein the Wnt/β-catenin active cancer is ovarian cancer.

13. The method of claim 1, wherein the Wnt/β-catenin active cancer is brain cancer.

14. The method of claim 1, wherein the Wnt/β-catenin active cancer is parathyroid cancer.

* * * * *

UNITED STATES PATENT AND TRADEMARK OFFICE
CERTIFICATE OF CORRECTION

PATENT NO. : 12,109,212 B2
APPLICATION NO. : 16/550993
DATED : October 8, 2024
INVENTOR(S) : William C. Hahn et al.

Page 1 of 1

It is certified that error appears in the above-identified patent and that said Letters Patent is hereby corrected as shown below:

In the Claims

In Column 33, Line 34 (Claim 4): the term "Wmt" should read --Wnt--.

Signed and Sealed this
Eleventh Day of March, 2025

Coke Morgan Stewart
*Acting Director of the United States Patent and Trademark Office*

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Chemically syntheized oligonucleotide

<400> SEQUENCE: 1
cctctttact cttgacacag cccat          25

<210> SEQ ID NO 2

```
<211> LENGTH: 25
<212> TYPE: DNA
<213> ORGANISM: Artificial Sequence
<220> FEATURE:
<223> OTHER INFORMATION: Chemically synthesized oligonucleotide

<400> SEQUENCE: 2
agcaacatta acaactcact ttagg                                              25
```